United States Patent [19]
Wilding et al.

[11] Patent Number: 5,726,026
[45] Date of Patent: *Mar. 10, 1998

[54] MESOSCALE SAMPLE PREPARATION DEVICE AND SYSTEMS FOR DETERMINATION AND PROCESSING OF ANALYTES

[75] Inventors: Peter Wilding, Paoli; Larry J. Kricka, Berwyn, both of Pa.

[73] Assignee: Trustees of the University of Pennsylvania, Philadelphia, Pa.

[*] Notice: The term of this patent shall not extend beyond the expiration date of Pat. No. 5,304,487.

[21] Appl. No.: 338,369

[22] Filed: Nov. 14, 1994

Related U.S. Application Data

[63] Continuation-in-part of Ser. No. 877,702, May 1, 1992, abandoned, Ser. No. 196,021, Feb. 14, 1994, Pat. No. 5,635,358, Ser. No. 250,100, May 26, 1994, abandoned, and Ser. No. 308,199, Sep. 19, 1994, Pat. No. 5,498,392, which is a continuation of Ser. No. 877,662, May 1, 1992, abandoned, said Ser. No. 196,021, is a division of Ser. No. 877,536, May 1, 1992, Pat. No. 5,304,487.

[51] Int. Cl.$^6$ ............... G01N 15/06; G01N 33/00; G01N 33/48; C12P 19/34
[52] U.S. Cl. ............... 435/7.21; 422/68.1; 422/50; 422/55; 422/58; 435/91.1; 435/91.2; 435/810; 436/527; 436/538; 436/807
[58] Field of Search ............... 422/68.1, 50, 55, 422/58; 435/7.1, 91.1, 91.2, 810; 436/527, 538, 807

[56] References Cited

U.S. PATENT DOCUMENTS

| | | |
|---|---|---|
| 3,799,742 | 3/1974 | Coleman. |
| 3,906,929 | 9/1975 | Augspurger. |
| 4,233,029 | 11/1980 | Columbus. |
| 4,302,313 | 11/1981 | Columbus. |
| 4,350,768 | 9/1982 | Tihon et al.. |

(List continued on next page.)

FOREIGN PATENT DOCUMENTS

| | | |
|---|---|---|
| 0320308 | 6/1989 | European Pat. Off.. |
| 0402995 | 12/1990 | European Pat. Off.. |
| 0430248 | 6/1991 | European Pat. Off.. |
| 0439182 | 7/1991 | European Pat. Off.. |
| 0483117 | 4/1992 | European Pat. Off.. |
| 2650657 | 2/1991 | France. |
| 3915920 | 11/1990 | Germany. |
| 400028771 | 2/1991 | Germany. |
| 2131972 | 7/1984 | United Kingdom. |
| 2191110 | 12/1987 | United Kingdom. |
| 2204398 | 9/1988 | United Kingdom. |
| WO9009596 | 8/1990 | WIPO. |
| WO9113338 | 9/1991 | WIPO. |
| WO9115750 | 10/1991 | WIPO. |
| WO9116966 | 11/1991 | WIPO. |

OTHER PUBLICATIONS

Hoopman, "Microchanneled Structures," in *Microstructures, Sensors and Actuators*, Cho et al., Eds., The American Society of Mechanical Engineers, 1990.

Kinosita et al., "Dual-view Microscopy with a Single Camera"; J. Cell Biol., 115(1): 67–73 (1991) (Abstract).

C. Schnaitman, "Cell Fractionation", Manual of Methods for General Bacteriology, 61: 52–55 (1981), American Society of Microbiology.

Anderson, *Nature*, 355: 379 (1992).

(List continued on next page.)

*Primary Examiner*—Christopher L. Chin
*Assistant Examiner*—Bao-Thuy L. Nguyen
*Attorney, Agent, or Firm*—Dann, Dorfman, Herrell and Skillman

[57] ABSTRACT

A mesoscale sample preparation device capable of providing microvolume test samples, separated into a cell-enriched fraction and a fraction of reduced cell content, for performing various analyses, such as binding assays, determinations involving polynucleotide amplification and the like. Analytical systems including such devices are also disclosed.

28 Claims, 7 Drawing Sheets

U.S. PATENT DOCUMENTS

| | | |
|---|---|---|
| 4,618,476 | 10/1986 | Columbus . |
| 4,676,274 | 6/1987 | Brown . |
| 4,790,640 | 12/1988 | Nason . |
| 4,886,761 | 12/1989 | Gustafson et al. . |
| 4,906,439 | 3/1990 | Grenner . |
| 4,908,112 | 3/1990 | Pace . |
| 4,911,782 | 3/1990 | Brown . |
| 4,963,498 | 10/1990 | Hillman et al. . |
| 4,999,283 | 3/1991 | Zavos et al. . |
| 5,110,745 | 5/1992 | Kricka et al. ............................ 436/87 |
| 5,114,858 | 5/1992 | Williams et al. . |
| 5,135,720 | 8/1992 | Uchida . |
| 5,147,606 | 9/1992 | Charlton et al. . |
| 5,176,203 | 1/1993 | Larzul . |
| 5,188,963 | 2/1993 | Stapleton . |
| 5,204,038 | 4/1993 | Heeger et al. ......................... 264/184 |
| 5,270,183 | 12/1993 | Corbett et al. . |
| 5,304,487 | 4/1994 | Wilding et al. ........................ 435/291 |
| 5,346,672 | 9/1994 | Stapleton et al. . |
| 5,427,946 | 6/1995 | Kricka et al. ........................... 435/291 |
| 5,486,335 | 1/1996 | Wilding et al. ........................... 422/55 |
| 5,498,392 | 3/1996 | Wilding et al. ........................ 422/68.1 |

OTHER PUBLICATIONS

Angell et al., *Scientific American*, 248: 44–45 (1983).
Appenzeller, *Science*, 254: 1300–1342 (1991).
Barany, *Proc. Natl. Acad. Sci.*, 88: 189–192 (1991).
Brown, "Development of a Stopped–Flow Cytometer," NSF Grant No. ISI 87–60730.
Brunette, *Exper. Cell Res.*, 167: 203–217 (1986).
Brunette, *Exper. Cell Res.*, 164: 11–26 (1986).
Columbus et al., *Clin. Res.*, 33: 1531–1537 (1987).
DeLuca et al., *Arch. Biochem. Biophys.*, 255: 285–292 (1983).
Dessy, *Chemometrics and Intelligent Laboratory Systems*, 8: 311 (1990), Abstract.
Esashi et al., "Integrated Flow Control Systems Fabricated on a Silicon Wafer," Proceedings, Electrochemical Society Conference, HI (Oct. 18–23, 1987) Electrochemical Society, Pennington, NJ., pp. 31–38B, 1987.
Fromherz eta l., *Biochimica et Biophysica Acta*, 1062: 103–107 (1991).
Goin et al., *Clin. Chem.*, 32: 1655–1659 (1986).
Haller in: *Solid Phase Biochemistry*, W.H. Scouten, Ed., John Wiley, New York, pp. 535–597 (1983).
Hanazato et al., *IEEE Transactions Electron Devices: ED33*: 47–51 (1986).
Howe et al., *IEEE Transactions Electron Devices, ED33*: 499–506 (1986).
Hung et al., *Med. & Biol. Engng.*, 9: 237–245 (1971).
Jonsson, *Methods in Enzymology*, 137: 381–389 (1988).
Kennedy et al., *Clin. Chem. Acta.*, 70: 1–31 (1976).
Kenny et al., *Appl. Phys. Lett.*, 58: 100–102 (1991).
Kikuchi et al., "Microchannels Made on Silicon Wafer for Measurement of Flow Properties of Blood Cells", *Biorheology*, 26: 1055 (1989), Abstract.
Kittilsland et al., *Journal de Physique*, 49(C4): 641–644 (1988).
Kittilsland et al., *Sensors and Activators*, A21–A23: 904–907 (1990).
Kricka et al., "Liquid Transport in Micron and Submicron Channels", *SPIE*, 1167: 159–168 (1989).
Kricka et al., *Clin. Chem.*, 26: 741–744 (1980).
LaCelle, *Blood Cells*, 112: 179–189 (1986).
Mandenius et al., *Anal. Biochem.*, 137: 106–114 (1984).
Mandenius et al., *Anal. Biochem.*, 170: 68–72 (1988).
Mandenius et al., *Methods in Enzymology*, 137: 388–394 (1988).
Manz et al., *Trends in Anal. Chem.*, 10: 144–149 (1991).
Masuda et al., *Proc. IEEE/IAS Meeting*, pp. 1549–1553 (1987).
McCartney et al., *Cancer Res.*, 41: 3046–3051 (1981).
Moghissi et al., *Am. J. Obstet. Gynecol.*, 114: 405 (1972).
Nakamura, *Immunochemical Assays and Biosensor Technology for the 1990's*, American Society of Microbiology, Washington, DC, pp. 205–215 (1992).
Nakamura et al., *Anal. Chem.*, 63: 268–272 (1991).
Parce et al., *Science*, 24: 243–247 (1989).
Rosenberg et al., *Clin. Chem.*, 30: 1462–1466 (1984).
Rosenberg et al., *Clin. Chem.*, 31: 1444–1448 (1985).
Sankolli et al., *J. Immun. Methods*, 104: 191–194 (1987).
Sato et al., *Sensors and Actuators*, A21–A23: 948–951 (1990).
Shoji et al., *Sensors and Actuators*, 15: 101–107 (1988).
Stange et al., *Biomaterials*, 9: 3–6 (1988).
Van Lintel, *Sensors and Actuators*, 15: 153–167 (1988).
Wallis et al., *J. Amer. Ceramic Soc.*, 53: 563–567 (1970).
Washizu et al., *Proceedings IEEE/IAS Meeting*, pp. 1735–1740 (1988).
Weissman et al., *Am. Inst. Chem. Eng. J.*, 17: 25–30 (1971).
Zemel et al. in: *Fundamentals and Applications of Chemical Sensors*, D. Schuetzle and R. Hammerle, Eds., ACS Symposium Series 309, Washington, DC, 1986, p. 2.
Biotrack, Ciba Corning, May, 1989.
Wilding, *Advanced Hospital Technology Laboratory*, pp. 38–42 (Oct. 1990).
Roche, On–Trak™, Sep. 1988.
Pfahler et al., "Liquid Transport in Micron and Submicron Channels", *Sensors and Actuators*, A21–23: 431–434 (1990).
Tracey et al., "Microfabricated Microhaemorheometer", *IEEE International Conference on Solid–State Sensors and Actuators*, pp. 82–84 (1991).
Washizu et al., "Handling of Biological Cells Using Fluid Integrated Circuit", *IEEE Industry Applications Society Annual Meeting*, 2: 1735–1740 (1988).
Backman, "Ligase Chain Reaction: Diagnostic Technology for the 1990's and Beyond", *Clin. Chem.*, 38: 457–458 (1992).
Chien et al., "Deoxyribonucleic Acid Polymerase from the Extreme Thermophile Thermus Aquaticus", *J. Bacteriol*, 127: 1550–1557 (1976).
Erlich, ed., "Principles and Applications for DNA Amplification," *PCR Technology*, Stockton Press, pp. 32–38 (1989).
Engelke et al., "Direct Sequencing of Enzymatically Amplified Human Genomic DNA", *Proc. Natl. Acad. Sci.*, 85: 544–548 (1988).
Farr et al., *Proc. Natl. Acad. Sci.*, 85: 1629–1633 (1988).
Higuchi et al., *Biotechnology*, 10: 413–417 (1992).
Kawasahi, "Sample Preparation from Blood, Cells and Other Fluids", *PCR Protocols*, Innis et al., eds., Academic Press, Inc., pp. 146–149 (1990).
Li et al., *Nature*, 335: 414–417 (1988).
Oste, "Polymerase Chain Reaction", *Biotechniques*, 6: 162–167 (1988).
Ou et al., *Science*, 239: 295–297 (1988).
Vener et al., *Anal. Biochem.*, 198: 308–311 (1991).
Walker et al., *Proc. Natl. Acad. Sci.*, 89: 392–396 (1992).
Wolf et al., *Nucl. Acids Res.*, 15: 2911–2927 (1987).

MESOSCALE SAMPLE PREPARATION DEVICE AND SYSTEMS FOR DETERMINATION AND PROCESSING OF ANALYTES

This application is a continuation-in-part of the following patent applications: U.S. application Ser. No. 07/877,702, filed May 1, 1992, abandoned in favor of U.S. application Ser. No. 08/347,498, filed Nov. 30, 1994, now U.S. Pat. No. 5,637,469; U.S. application Ser. No. 08/196,021, filed Feb. 14, 1994, now U.S. Pat. No. 5,675,358, as a divisional of U.S. Ser. No. 07/877,536, filed May 1, 1992 now U.S. Pat. No. 5,304,487; U.S. application Ser. No. 08/250,100, filed May 26, 1994 and abandoned in favor of U.S. application Ser. No. 08/427,493 filed Apr. 24, 1995, now U.S. Pat. No. 5,486,335; (which is a continuation of Ser. No. 07/877,536, filed May 1, 1992, now U.S. Pat. No. 5,304,487) and U.S. application Ser. No. 08/308,199, which was filed Sep. 19, 1994 as a file wrapper continuation of U.S. application Ser. No. 07/877,662, filed May 1, 1992, now abandoned, and which is now U.S. Pat. No. 5,498,392. The entire disclosures of the aforementioned patents and patent applications are incorporated by reference herein.

BACKGROUND OF THE INVENTION

This invention relates to sample preparation devices having small dimensions for facilitating the efficient preparation of microvolume test samples, e.g., of whole blood, for the determination and/or processing of analytes present therein. The present invention also relates to test systems including such devices, together with devices of similar dimensions which are designed, for example, to perform various assay protocols as well as analyses involving amplification of pre-selected polynucleotides, such as polymerase chain reaction (PCR).

In recent decades the art has developed a large number of protocols, test kits, and devices for conducting analyses on biological samples for various diagnostic and monitoring purposes. Immunoassays, immunometric assays, agglutination assays, analyses involving polynucleotide amplification reactions, various ligand-receptor interactions, and differential migration of species in a complex sample all have been used to determine the presence or quantity of various biological molecules or contaminants, or the presence of particular cell types.

Recently, small, disposable devices have been developed for handling biological samples and for conducting certain clinical tests. Shoji et al. reported the use of a miniature blood gas analyzer fabricated on a silicon wafer. Shoji et al., Sensors and Actuators, 15: 101–107 (1988). Sato et al. reported a cell fusion technique using micromechanical silicon devices. Sato et al., Sensors and Actuators, A21–A23: 948–953 (1990). Ciba Corning Diagnostics Corp. (USA) has manufactured a microprocessor-controlled laser photometer for detecting blood clotting.

Micromachining technology originated in the microelectronics industry. Angell et al., Scientific American, 248: 44–55 (1983). Micromachining technology has enabled the manufacture of microengineered devices having structural elements with minute dimensions, ranging from tens of microns (the dimensions of biological cells) to nanometers (the dimensions of some biological macromolecules). Most experiments reported to date involving such small structures have involved studies of micromechanics, i.e., mechanical motion and flow properties. The potential capability of such devices has not been exploited fully in the life sciences.

Brunette (Exper. Cell Res., 167: 203–217 (1986) and 164: 11–26 (1986)) studied the behavior of fibroblasts and epithelial cells in grooves in silicon, titanium-coated polymers and the like. McCartney et al. (Cancer Res., 41: 3046–3051 (1981)) examined the behavior of tumor cells in grooved plastic substrates. LaCelle (Blood Cells, 12: 179–189 (1986)) studied leukocyte and erythrocyte flow in microcapillaries to gain insight into microcirculation. Hung and Weissman reported a study of fluid dynamics in micromachined channels, but did not produce data associated with an analytical device. Hung et al., Med. and Biol. Engineering, 9: 237–245 (1971); and Weissman et al., Am. Inst. Chem. Eng. J., 17: 25–30 (1971). Columbus et al. utilized a sandwich composed of two orthogonally orientated v-grooved embossed sheets in the control of capillary flow of biological fluids to discrete ion-selective electrodes in an experimental multi-channel test device. Columbus et al., Clin. Chem., 33: 1531–1537 (1987). Masuda et al. and Washizu et al. have reported the use of a fluid flow chamber for the manipulation of cells (e.g., cell fusion). Masuda et al., Proceedings IEEE/IAS Meeting, pp. 1549–1553 (1987); and Washizu et al., Proceedings IEEE/IAS Meeting, pp. 1735–1740 (1988). The art has not fully explored the potential of using microengineered devices for the determination of analytes in fluid samples, particularly in the area of biological analyses.

Biological analyses utilizing polynucleotide amplification techniques are well known (See e.g., Maniatis et al., Molecular Cloning: A Laboratory Manual, Cold Spring Harbor Laboratory Press, 1989, pp. 14.1–14.35). One such technique is PCR amplification, which can be performed on a DNA template using a thermostable DNA polymerase, e.g., Taq DNA polymerase (Chien et al., J. Bacteriol., 127: 1550 (1976)), nucleoside triphosphates, and two oligonucleotides with different sequences, complementary to sequences that lie on opposite strands of the template DNA and which flank the segment of DNA that is to be amplified ("primers"). The reaction components are cycled between a higher temperature (e.g., 94° C.) for dehybridizing double stranded template DNA, followed by lower temperatures (e.g., 65° C.) for annealing and polymerization. A repeated reaction cycle between dehybridization, annealing and polymerization temperatures provides approximately exponential amplification of the template DNA. Machines for performing automated PCR chain reactions using a thermal cycler are available (Perkin Elmer Corp.)

PCR amplification has been applied to the diagnosis of genetic disorders (Engelke et al., Proc. Natl. Acad. Sci., 8.5: 544 (1988), the detection of nucleic acid sequences of pathogenic organisms in clinical samples (Ou et al., Science, 239: 295 (1988)), the genetic identification of forensic samples, e.g., sperm (Li et al., Nature, 335: 414 (1988)), the analysis of mutations in activated oncogenes (Farr et al., Proc. Natl. Acad. Sci., 85: 1629 (1988)) and in many aspects of molecular cloning (Oste, BioTechniques, 6: 162 (1988)). PCR assays can be used in a wide range of applications such as the generation of specific sequences of cloned double-stranded DNA for use as probes, the generation of probes specific for uncloned genes by selective amplification of particular segments of cDNA, the generation of libraries of cDNA from small amounts of mRNA, the generation of large amounts of DNA for sequencing, and the analysis of mutations. There is a need for convenient, rapid systems for performing polynucleotide amplification, which may be used clinically in a wide range of potential applications in clinical tests such as tests for paternity, and for genetic and infectious diseases.

Current analytical techniques utilized for the determination of microorganisms are rarely automated, usually require incubation in a suitable medium to increase the number of organisms, and generally employ visual and/or chemical methods to identify the strain or sub-species of interest. The inherent delay in such methods frequently necessitates medical intervention prior to definitive identification of the nature of an infection. In industrial, public health or clinical environments, such delays may have unfortunate consequences. There is a need for convenient systems for the rapid detection of microorganisms.

It is an object of the present invention to provide sample preparation devices for use with related analytical devices which enable rapid and efficient analysis of sample fluids, based on very small volumes, and determination of substances present therein at very low concentrations. Another object is to provide easily mass produced, disposable, small (e.g., less than 1 cc in volume) devices having microfabricated structural elements capable of facilitating rapid, automated analyses of preselected molecular or cellular analytes, including intra-cellular molecules, such as DNA, in a range of biological and other applications. It is a further object of the invention to provide a variety of such devices that individually can be used to implement a range of rapid clinical tests, e.g., tests for viral or bacterial infection, genetic screening, sperm motility, blood parameters, contaminants in food, water, or body fluids, and the like.

SUMMARY OF THE INVENTION

The present invention provides a microfabricated sample preparation device which conveniently provides microvolume fractions of test sample comprising particulate components, e.g., cells, for various biological and other analyses. The invention further provides analytical systems which include the microfabricated sample preparation device of the invention together with a microfabricated analyte detection device, e.g., an immunoassay device, and/or a microfabricated device for carrying out polynucleotide amplification.

The sample preparation device of the present invention comprises a sample flow passage having a sample inlet and an outlet in fluid communication and a separator disposed between the inlet and the outlet. The separator has an upstream-facing portion defining a separation zone in the flow passage in which particulate components present in the sample fluid are collected. The device preferably comprises a flow channel in fluid communication with the separation zone which affords discharge of collected particulate components from the separation zone. The flow channel has an inlet section for directing a carrier fluid into the separation zone and over the upstream-facing portion of the separator and a discharge section for directing the carrier fluid from over the upstream-facing portion of the separator and out of the separation zone. At least one of the flow passage and the flow channel sections has at least one mesoscale dimension, as characterized below.

According to one embodiment of the invention, the flow passage has at least one mesoscale dimension and the separator comprises a region of restricted flow in the flow path, which is formed by at least one passageway having at least one mesoscale dimension that is smaller than the least mesoscale dimension of the flow passage and sufficiently small to separate particulate components from the sample fluid.

The sample preparation device of the invention can be made using known microfabrication techniques, with the flow passage and the flow channel being formed in a surface of a solid substrate. In a preferred embodiment, the surface of the substrate in which the structural elements are formed is enclosed by a cover, such as a transparent glass or plastic cover, adhered to such surface.

The mesoscale sample preparation device of the present invention is specially adapted for use in conjunction with the mesoscale detection devices which are the subject of co-pending U.S. Ser. No. 07/877,702, abandoned in favor of U.S. application Ser. No. 08/347,498 and/or the mesoscale polynucleotide amplification devices which are the subject of co-pending U.S. application Ser. No. 08/308,199, now U.S. Pat. No. 5,498,392. The full disclosures of the '702 and '199 applications are incorporated by reference in the present application, as if set forth herein in full, as previously noted.

The mesoscale devices described above can be used in various combinations to function as an analytical system, as will be described in further detail below. In one embodiment, the devices may be utilized for analyses of a cell-containing test sample. The test sample fractions provided by the sample preparation device of the present invention may be analyzed serially or essentially simultaneously.

The mesoscale detection devices, which enable the determination of various analytes of interest, comprise a solid substrate microfabricated to define a sample inlet port and a mesoscale flow system which includes an analyte detection region in fluid communication with the inlet port and, optionally, a sample flow channel interconnecting the inlet port and the analyte detection region. At least one of the analyte detection region and the sample flow channel, when present, has at least one mesoscale dimension. The analyte detection region is provided with a reagent which interacts with the analyte of interest, resulting in a detectable product which is determinative of the analyte. In one embodiment, the reagent is a binding substance, optionally immobilized in the detection region, either on a stationary or mobile support, for specifically binding the analyte. Also included is a detector for detecting the aforementioned product, which allows determination of the analyte in the test sample.

The mesoscale polynucleotide amplification device comprises a solid substrate that is microfabricated to define a sample inlet port and a mesoscale flow system, which includes a polynucleotide amplification region in fluid communication with the inlet port of the devices, and, optionally, a flow channel interconnecting the inlet port and the polynucleotide amplification region. At least one of the polynucleotide amplification region and the sample flow channel, when the latter is present, has at least one mesoscale dimension. Lysing means is also provided in a sample flow channel upstream of the polynucleotide amplification region for lysing cell components of a biological test sample. Such devices may be utilized to implement PCR, in which case the polynucleotide amplification region contains appropriate reagents and means is provided for thermally cycling the reagents, such that, in each cycle, the temperature is controlled to dehybridize double stranded polynucleotides, anneal the primers to single stranded polynucleotide, and synthesize amplified polynucleotide between the primers.

The individual analytical devices described herein are within the scope of the present invention, whether or not they are used in conjunction with the sample preparation device of the invention.

The devices described above will normally be used with an appliance that functions as a holder for the devices and which mates one or more ports on the devices with one or more flow lines in the appliance. A test sample, such as whole blood, containing an analyte of interest may be applied to the inlet of the sample preparation device after which an impellent, such as a pump, which may be incorporated in the appliance or in the device itself, is employed to cause the sample to flow along the flow passage and through the separation zone. Test sample which is free of particulate components is transferred from the sample preparation device to the analyte detection device, the outlet of the former being in fluid communication with the inlet port of the latter. Particulate components, such as blood cells or other formed bodies, remaining in the separation zone can be discharged from the separation zone, and transferred to the polynucleotide amplification device via the discharge section of the flow channel of the sample preparation device, which is in fluid communication with the inlet port of the polynucleotide amplification device. Alternatively, the test sample may be injected into the sample preparation device, or the sample may enter the mesoscale sample preparation device through the inlet by capillary action. Optionally, depending on the analytical protocol being carried out in the devices described above, the appliance may also be designed to inject into the devices reagents, such as labelled binding substances, polynucleotide amplification reagents, buffers, or any other reagent required to carry out the desired analysis.

The device and systems of the invention may be used to implement a variety of automated, sensitive and rapid clinical tests including the analysis of cells or molecules or for monitoring reactions or cell growth. Essentially any test involving determination of the presence or concentration of a molecular or ionic analyte, the presence of a particular cell type or the presence of a gene or recombinant DNA sequence in a cell can be implemented to advantage using the device and analytical systems of the present invention. These mesoscale devices can provide a rapid chemical test for the detection of pathogenic bacteria or viruses. The devices can also provide a rapid test for the presence or concentration of blood constituents, such as hormones. Additional useful applications include, but are not limited to, a range of other biological assays, such as blood type testing.

The device and systems of the invention may be readily sterilized prior to use. Tests performed using the device and systems of the invention may be completed rapidly, and at the conclusion of the test the devices can be discarded, which beneficially prevents contamination between samples, entombs potentially hazardous material, produces only microvolumes of waste fluid for disposal and enables inexpensive analyses.

Additional advantages and features of the present invention are set forth in, and will be apparent to those skilled in the art from the detailed description of the invention presented below, considered in conjunction with the accompanying drawings.

BRIEF DESCRIPTION OF THE DRAWINGS

FIG. 6A shows the devices abutting end-to-end; and FIG. 6B shows a stacked arrangement of the devices.

FIG. 8B shows a similar design for performing enzyme immunoassays and having dual capture chambers. An analyte of interest, such as a protein, may be captured in the first chamber, e.g., by a suitable immunocapture reagent, labelled with an antibody-enzyme conjugate and exposed to a chromogenic substrate. The enzyme converts the substrate to a chromophore which is captured, e.g., by a suitable immunocapture reagent, in the second chamber which concentrates the chromophore and reduces background signal. The second chamber may optionally be used for detection of the chromophore, as well.

As seen in FIG. 9A, a single chamber is provided for capture and detection of the analyte of interest.

Like reference characters designate like parts in the drawing figures in which they appear.

DETAILED DESCRIPTION OF THE INVENTION

Figure 5:
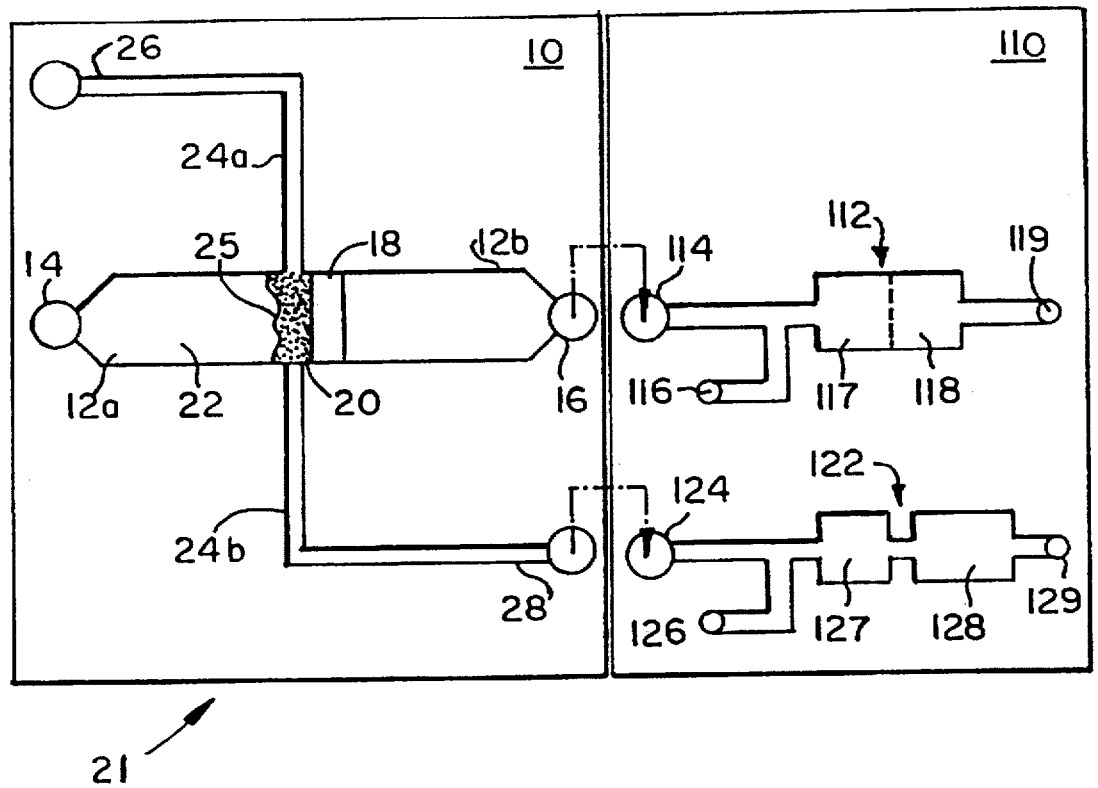
FIG. 5 is a plan view of a diagrammatic representation of the same device shown in FIG. 1, the respective outlets of which are in fluid communication with first and second microfabricated analytical structures which are designed to perform separate analyses on the sample fractions provided by the sample preparation device.

The sample preparation device of the invention comprises a solid substrate, preferably in the form of a chip having dimensions on the order of less than one to a few millimeters thick and approximately 0.1 to 0.5 centimeters square. The substrate is microfabricated to form a sample flow passage having an inlet and an outlet as well as a separator disposed intermediate to the inlet and outlet. The upstream-facing portion of the separator defines a separation zone in the flow path in which particulate components of the test sample are collected. The device may also include a flow channel in fluid communication with the separation zone which functions to discharge collected particulate components from the separation zone. The flow channel has an inlet section for directing a carrier fluid into the separation zone and over the upstream-facing portion of the separator and a discharge section for directing the carrier fluid, in which the particulate components are entrained, out of the separation zone. At least one of the aforementioned flow passage and flow channel sections have at least one mesoscale dimension.

If the particulate components of the sample are not to be analyzed, they can remain in the separation zone, in which case the flow channel is essentially nonfunctional and thus may be eliminated from the device.

As used herein, the term "mesoscale" refers to flow passages or channels and other structural elements, e.g. reaction and/or detection chambers, at least one of which has at least one cross-sectional dimension on the order of 0.1 µm to 1000 µm and more preferably 0.2 µm to 500 µm. The preferred depth of the flow passages and chambers is on the order of 0.1–100 µm and more preferably 2–50 µm. The preferred flow passage width is on the order of 2–200 µm and more preferably 3–100 µm. The preferred chamber width is on the order of 0.05–5 mm and more preferably 50–500 µm. The width of the passageway(s) in the separator is typically on the order of less than 50 µm which is sufficiently small to separate particulate matter from most biological samples and other test samples of interest. The separator passageways will normally have a depth of about 0.1 to about 100 µm. The length of the separator passageways will typically be within the range of about 0.1 µm to about 5 mm.

The flow passages and other structures, when viewed in cross-section, may be triangular, ellipsoidal, square, rectangular, circular or any other shape at least one cross-sectional dimension of which, transverse to the path of flow of sample fluid through or into a given structure, is mesoscale.

The mesoscale devices of the invention facilitate sample preparation in a broad range of biological analyses and, together with the analytical devices described herein, enable the rapid determination of microquantities of both molecular and cellular analytes in various test samples. At the conclusion of the analysis, the devices typically are discarded.

Mesoscale devices having at least one flow passage or other structural element with at least one mesoscale dimension can be designed and fabricated in large quantities from a solid substrate material using various micromachining methods known to those skilled in the art. Such methods include film deposition processes, such as spin coating and chemical vapor deposition, laser machining or photolithographic techniques, e.g. UV or X-ray processes, etching methods which may be performed by either wet chemical processes or plasma processes, LIGA processing or plastic molding. See, for example, Manz et al., *Trends in Analytical Chemistry* 10: 144–149 (1991).

The sample preparation device of the invention may be conveniently constructed by forming the flow passages and separator in the surface of a suitable substrate and then mounting a cover over such surface. The solid substrate and/or cover may comprise a material such as silicon, polysilicon, silica glass, thermocouple materials, gallium arsenide, polyimide, silicon nitride and silicon dioxide. The cover and/or substrate may also comprise a plastic material, such as acrylic, polycarbonate, polystyrene, polyethylene or other resin materials. Optionally, the cover and/or substrate may comprise a transparent material, e.g., a relatively thin, anodically bonded layer of glass or ultrasonically welded plastic sheet material. Alternatively, two substrates of like material can be sandwiched together, or a suitable substrate material may be sandwiched between two transparent cover layers.

Figure 1:
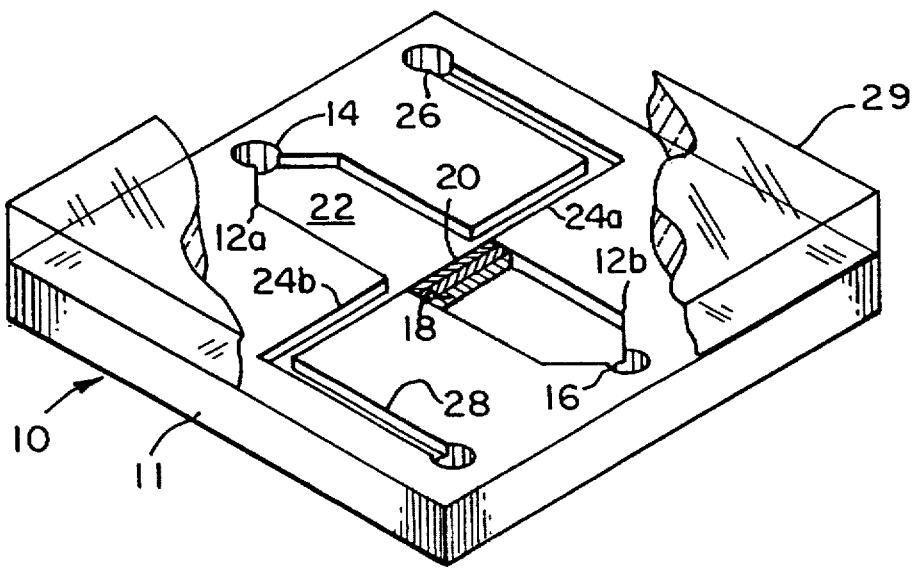
FIG. 1 is a perspective view of a diagrammatic representation of a sample preparation device of the invention, as seen through a transparent cover.

A diagrammatic representation of one embodiment the mesoscale sample preparation device of the invention is shown in FIG. 1. The device 10 is microfabricated in a suitable substrate 11, thereby forming a sample flow passage 12a and 12b having sample inlet port 14 and outlet port 16. A filter-type separator 18 is interposed in the flow passage between inlet 14 and outlet 16. The upstream-facing portion 20 of the separator defines a separation zone 22 for collecting particulate components of the test sample. The device also includes a flow channel 24a and 24b in fluid communication with separation zone 22 for delivering a carrier fluid to, and discharging collected particulate matter from the separation zone. Flow channel 24a, 24b has an inlet section 26 for directing carrier fluid, e.g., isotonic buffer, from a source (not shown) over the upstream-facing portion 20 of separator 18. Discharge section 28 conveys the carrier fluid from over the upstream-facing surface of the filter element and out of separation zone 22.

Separator 18 which is microfabricated in sample flow passage 12a and 12b of the sample preparation device serves to remove particulate matter from the test sample passed through the device prior to analysis. In one embodiment, shown in FIGS. 2 and 3, the separator comprises a series of mesoscale passageways of reduced dimension in comparison with flow passage 12a, 12b. In operation, separator 18 functions as a filter, accumulating particulate matter on its upstream surface 18a, while the filtrate exiting passageways 19 continues along flow passage 12b. The filter passageways 19 are microfabricated with depths and widths on the order of about 5 μm to about 50 μm, whereas flow passage 12a, 12b have maximum depths and widths on the order of approximately 1000 μm. The filter element is preferably microfabricated in the substrate of the device so as to form at least one, and preferably several, generally upstanding projections of the substrate material disposed in the flow passage which serve to restrict the flow of sample fluid through the separation zone.

Figure 2:
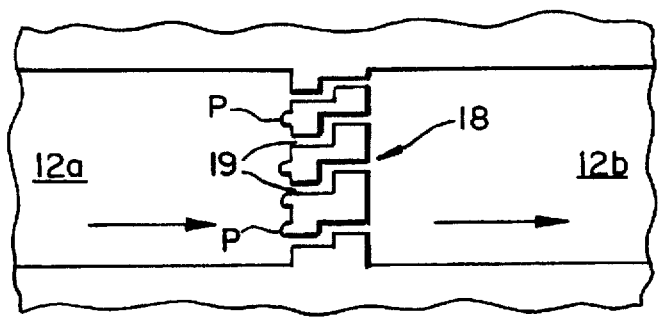
FIGS. 2 and 3 show fragmentary plan views of different embodiments of a microfabricated restricted flow (filter-type) separator within the flow passage through a portion of a sample preparation device, the separator having a series of passageways restricting flow of the test sample through the flow passage.
Figure 3:
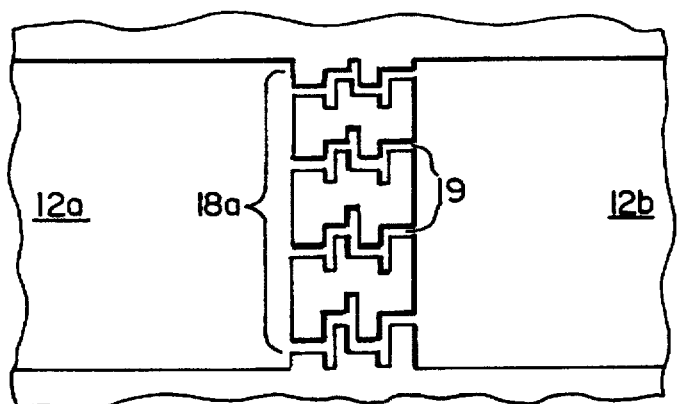

Protuberances p may be provided on the exterior of the upstream-facing portion of separator 18, as depicted in FIG. 2, as an aid in preventing plugging of passageways 19 by particulate matter in the sample fluid. Also, a sump (not shown) may be provided adjacent the upstream-facing portion of separator 18 for collecting insoluble debris removed from the sample fluid.

Separator 18 preferably is an essentially stationary structure permanently positioned between sample inlet 14 and outlet 16 of the flow passage, as can be seen in FIG. 1. Alternatively, however, the separator may be transiently disposed in the flow passage. For example, a mass of magnetic particles may be retained in relatively fixed position in flow passage 12a, 12b by means of an applied magnetic field to effect filtration of particulate matter from the test sample. The fluid portion of the sample passes through the void spaces between the particles as the filtrate. At the appropriate time, the applied magnetic field is removed and the magnetic particles may be transferred from the flow passage, together with any particular matter from the test sample accumulated thereon, for analysis or disposal, as desired.

Separator 18 may, if desired, comprise a reagent that facilitates removal of particles or formed bodies from the test sample. In the case of a biological sample comprising a mixed cell population, for example, a binding substance that releasably binds to a specific target cell type within the mixed population may be adsorbed or otherwise affixed to the separator to effect removal and selective retention of the target cell type. Cells which are not retained can be conveyed from the separation zone for disposal. The retained cells are subsequently caused to be released for analysis.

Figure 4:
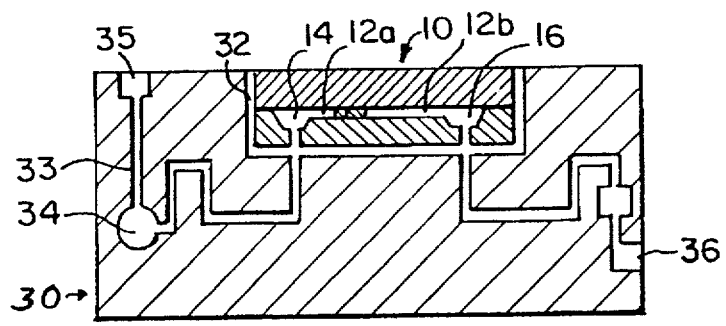
FIG. 4 is a schematic illustration, in cross-section, of a sample preparation device of the invention combined with an appliance which serves to hold the device and to regulate fluid flow through the device.

The sample preparation device of the invention can be used in combination with an appliance, such as appliance 30, shown in schematic cross-section in FIG. 4, for delivering fluids to, discharging fluids from, and transferring fluids between the different devices constituting the analytical systems of the invention. Appliance 30, which has a nesting site 32 for holding the device 10, and for registering ports, e.g. port 14 on the device, with a flow line 33 in the appliance. The appliance may include an impellent, such as pump 34 shown in FIG. 4, for conveying the sample through the flow passages of the device. After a biological fluid sample suspected to contain a particular analyte of interest is applied to the inlet port 35 of the appliance, pump 34 is actuated to convey the sample into port 14 of device 10 and then through flow passage 12a,12b. Although pump 34 is shown as an element of appliance 30, it may, if desired be incorporated into device 10 according to known microfabrication techniques. Economic considerations, however, favor placement of the pump in appliance 30. Alternatively, depending on the nature of the analyses to be performed, a sample may be injected into the device, or the sample may enter the flow passages of the device through the inlet port by capillary action. In another embodiment, the appliance may be disposed over the sample preparation chip, and may be provided with a flow line communicating with the inlet port in the device, e.g., in the absence of a cover over the device, to allow a sample to be injected into the device. The microfabricated structures of the devices may be filled to a hydraulically full volume and the appliance may be utilized to direct the flow of fluid through the structures, e.g., by means of valves located in the device or in the appliance. The incorporation of valves in a microfabricated silicon chip can be accomplished according to techniques known in the art.

The outlet 36 of appliance 30 may be interconnected to the inlet of a similar appliance holding an analytical device of the type described herein, whereby the sample prepared in device 10 is transferred to the analytical device for testing.

The analytical devices also may be utilized in combination with an appliance for viewing the contents of the mesoscale flow passages and other structures in the devices. For example, the appliance may comprise a microscope (not shown) for viewing the contents of the mesoscale structure (s) in the device. Transparent cover 29, as shown in FIG. 1, serves as a window which facilitates dynamic viewing of the contents of the device.

FIG. 5 shows a diagrammatic representation of the combination of the sample preparation device of FIG. 1 and analytical device 110 designed to carry out various binding assay protocols, and also polynucleotide amplification. To this end the device 110 is provided with an assay structure 112 and a polynucleotide amplification/assay structure 122. In the embodiment illustrated in FIG. 5, the outlet of flow passage 12a, 12b is in fluid communication with the inlet port 114 of assay structure 112 of the device; and the discharge section 28 of channel 24a, 24b is in fluid communication with the inlet port 124 of polynucleotide amplification/assay structure 122. Reagents used in performing the assay or other test or analysis may be introduced through reagent inlet ports 116 or 126, respectively. A reaction region 117 is typically provided in assay structure 112 in which a suitable reagent interacts with the analyte to yield a detectable product which is determinative of the analyte. That is to say, the product produced is one which provides definite information as to the nature or quantity of the analyte. The product may be detected in the form in which it is produced in reaction region 117, or it may be subject to further reaction to enhance its detection. A separate reaction/detection region 118 may be provided for this purpose.

A solution containing analyte-specific binding substances may be introduced into reaction region 117 via an inlet port (not shown) in fluid communication with the reaction region. Protein binding substances introduced in aqueous solution may be retained in a mesoscale structure in lyophilized form. Alternatively, binding substances may be immobilized in a mesoscale chamber of the analytical devices after its manufacture by, for example, physical adsorption or chemical attachment to the surface of the chamber or to a mobile, solid phase support, such as magnetic or non-magnetic polymer particles disposed in the chamber.

In carrying out polynucleotide amplification using device 110, cells of interest transferred from discharge section 28 of the sample preparation device 10 are subject to lysis either by a lysing agent or by a lysing structure as described in the above-mentioned U.S. Pat. No. 5,304,487. The target polynucleotide released from the cells undergoes amplification in amplification region 127 and the amplified polynucleotide may be detected in detection region 128. One or more of the apertures 116, 119, 126 and 129 may be open to the atmosphere to vent the system(s). The operation of the binding assay structure 112 and the polynucleotide amplification/assay structure 122 will be further explained with reference to other embodiments of such devices described below.

Although assay structure 112 and polynucleotide amplification/assay structure 122 are fashioned on a common substrate as a single device, as shown in FIG. 5, the structures may be fabricated on separate substrates and function as distinct analytical devices or chips, as will appear below.

Figure 6A:
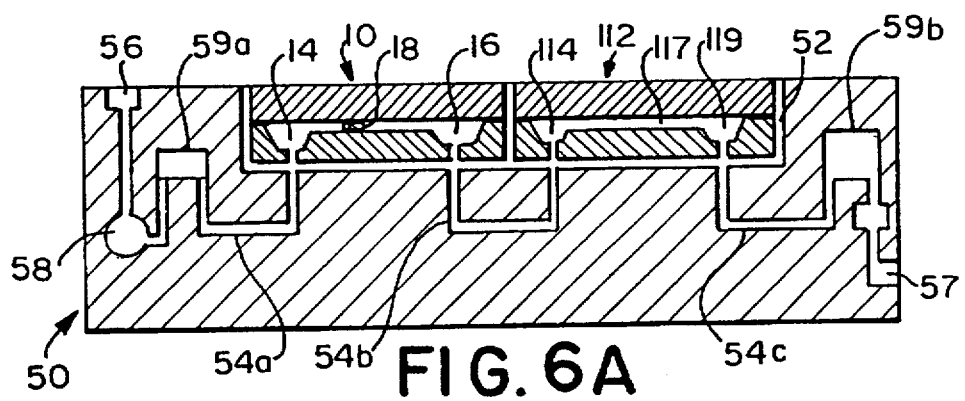
FIGS. 6A and 6B are schematic illustrations, in cross-section, of a sample preparation device of the invention with the outlet of the flow passage from the separation zone in fluid communication with the sample inlet of an analytical device for implementing various assay protocols. Both devices are shown in combination with an appliance which serves to hold the devices, regulate fluid flow through the devices, and, in the embodiment shown in FIG. 6A, detect pressure differentials at preselected locations along the course of fluid flow through the devices.
Figure 6B:
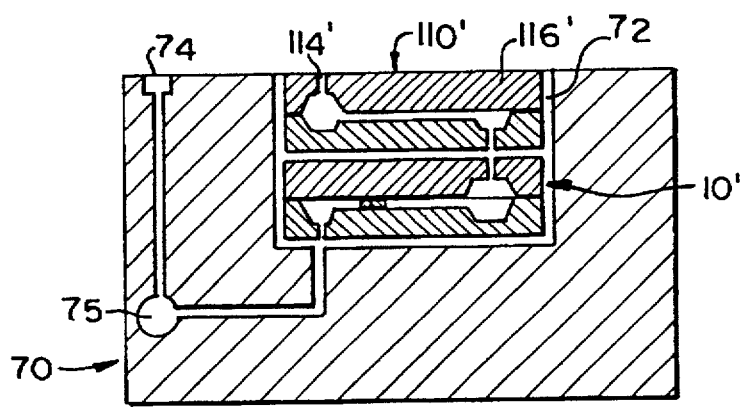
Figure 7:
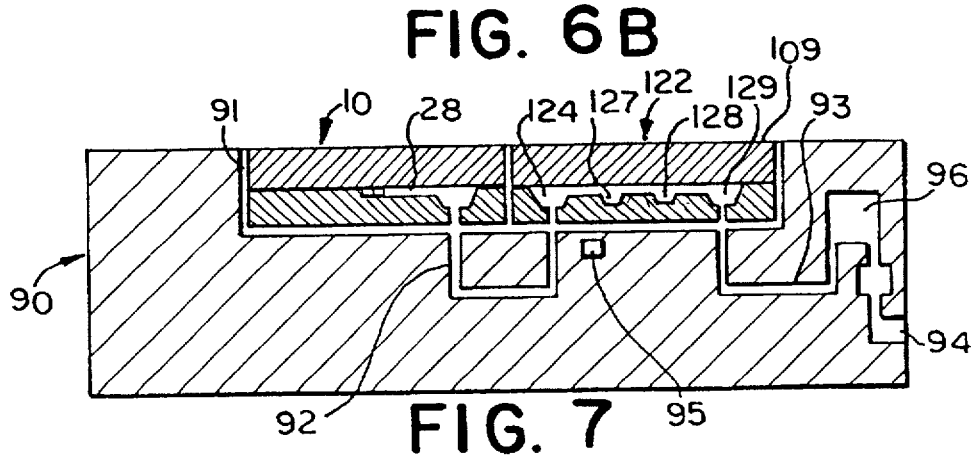
FIG. 7 is a schematic illustration, in cross-section, of a sample preparation device of the invention with the outlet of the carrier fluid flow channel in fluid communication with the sample inlet of an analytical device for performing polynucleotide amplification. Both devices are shown in combination with an appliance which serves to hold the devices, regulate fluid flow through the devices and detect pressure differentials at preselected locations along the course of fluid flow through the devices.

When the sample preparation device and analytical devices described above are used together to function as a analytical system, as illustrated in FIG. 5, for example, the system is advantageously combined with an appliance of the type depicted in FIGS. 6A, 6B and 7. Like the appliance of FIG. 4, previously described, appliance 50 in FIG. 6A serves to deliver fluid to, discharge fluid from, and transfer fluid between the respective devices. Appliance 50 has a nesting site 52 for holding sample preparation device 10 and analytical device 112 and for registering ports in the devices with flow lines in the appliance. Specifically, flow line 54a is in registry with inlet port 14 of the sample preparation device, flow line 54b is in registry both with outlet 16 of the sample preparation device and inlet 114, and flow line 54c is in registry with outlet 119 of assay structure 112 of the analytical device. As illustrated in FIG. 6A, flow line 54a is in fluid communication with appliance inlet port 56, whereas flow line 54C is in fluid communication with appliance outlet 57. The appliance typically includes an impellent, such as pump 58, for forcing sample fluid through the analytical system. After applying to inlet port 56 of appliance 50, a particle-containing fluid test sample, e.g., whole blood, the serum phase of which is suspected to contain an analyte of interest, pump 58 is actuated to force the sample through separator 18, providing sample fluid, e.g., serum, of substantially reduced particle content. The substantially particle-free sample fluid is transferred from device 10 via flow line 54B to assay structure 112 for testing, e.g., immunoassay.

The binding of analyte, per se, or analyte reaction products to a binding substance in the reaction/detection region of the analytical devices can be detected by any number of methods, including monitoring the pressure or electrical conductivity of sample fluids in the device(s), as disclosed in the above-referenced related applications (see, for example, U.S. Ser. No. 877,702, abandoned in favor of U.S. application Ser. No. 08/347,498), or by optical detection through a transparent cover, either visually or by machine. For example, reaction of an analyte with a binding substance in the reaction region 117 of analytical device 112 illustrated in FIG. 6A can be detected by monitoring the pressure of the sample fluids in certain regions of the mesoscale flow passages. This is accomplished in the analytical system-appliance combination of FIG. 6A by means of two pressure detectors 59a and 59b for detecting flow pressure of fluids entering and exiting the devices through ports 14 and 119, respectively. When, during the performance of an assay, particles agglomerate or molecules chemically interact to form a network causing restricted flow or an increase in the viscosity of the sample liquid passing through the reaction/detection region, such changes can be detected as a pressure change which is indicative of a positive result. Mesoscale pressure sensors, and other electrical or electro-mechanical sensors can be directly fabricated on a silicon substrate and can be mass-produced according to well established techniques. Angell et al., Scientific American, 248: 44–55 (1983).

Other embodiments of appliances may be fabricated for use in carrying out different assay protocols with different devices in accordance with the present invention. One such embodiment is depicted in FIG. 6B, which illustrates a cross sectional view of an analytical system, comprising analyte device 110' stacked upon a sample preparation device 10', disposed in nesting site 72 provided in appliance 70. A particle-containing test sample fluid is applied to appliance sample inlet 74, whereupon an impellent, such as pump 75, causes the sample fluid to pass through device 10, providing a sample fluid of substantially reduced particle content for analysis in analytical device 110'. The cover 116' of analytical device 110' has an aperture 114' open to the atmosphere to vent the system. Placement of the analytical device 110' on the top of the stack allows optical detection through a transparent portion of cover 116'.

A separate view of an analytical system, comprising a sample preparation chip and an analytical device for polynucleotide amplification, in combination with an appliance of the type described above is provided in FIG. 7. The cross-sectional view of the analytical system in FIG. 7 shows appliance 90 having a nesting site occupied by sample preparation device 10 and the polynucleotide amplification/assay structure 122. The discharge section 28 of flow channel 24b in sample preparation device 10 is in fluid communication, through flow line 92 with the inlet port 124 of polynucleotide amplification/assay structure 122. Flow line 93 is in registry with outlet 129 of the analytical device and in fluid communication with appliance outlet 94.

The polynucleotide sample, after release from the cell component separated from the sample fluid in sample preparation device 10, e.g., by contacting with the suitable lysing means as described above, is introduced into amplification region 127. Reagents required for amplification are also added to amplification region 127 through inlet 126, as shown in FIG. 5. An impellent, such as a pump (not shown), is used to deliver the polynucleotide sample through flow line 92 to amplification region 127.

Amplification reagents may be similarly delivered to amplification region 127 through a different flow line provided in the appliance or in the analytical device (not shown). The product of the polynucleotide amplification reaction may be transferred to region 128 for detection in the manner previously described. The resultant product may be recovered, if desired, through appliance outlet 94.

Pressure differentials along the path of flow of the test sample fluid through devices 10 and 122 may be measured using pressure sensor 96 in conjunction with a pressure sensor (not shown) deployed in the appliance or the device to measure pressure at a point upstream of discharge section 28 of device 10.

Appliance 90 may include a heating/cooling element 95 for controlling the temperature within the polynucleotide amplification region, e.g., an electrical heating element and/or a refrigeration element. An electrical heating element (not shown) may alternatively be integrated into the substrate of analytical device 122, with electrical elements for power mated to matching electrical contacts in the appliance below the amplification region 127. Alternatively, the appliance may include an internal or external heating means, such as a laser or other source of electromagnetic energy (not shown) disposed adjacent amplification region 127 of polynucleotide amplification/assay structure 122. A microprocessor in appliance 90 may be used to regulate the heating element in order to provide a temperature cycle in the polynucleotide amplification region between a temperature suitable for dehybridization, e.g., 94° C., and temperatures suitable for annealing and polymerization, e.g., 65° C. A thermocouple may also be provided in the substrate surrounding amplification region 127 in electrical contact with the appliance to allow microprocessor or other electronic controller to detect and maintain the temperature cycles in the reaction chamber. A cooling element, such as a miniature thermoelectric heat pump (Materials Electronic Products Corp., Trenton, N.J.), may also be included in the appliance for adjusting the temperature of the amplification chamber. In another embodiment, the temperature of the polynucleotide amplification chamber can be regulated by a timed laser pulse directed at the reaction chamber through glass cover 109, so as to allow sequential heating and cooling of the sample to the required temperatures for the amplification cycle. The thermal properties of silicon enable a rapid heating and cooling cycle.

In all of the embodiments of the invention depicted in FIGS. 4, 6A, 6B and 7, the pump may be subject to control by a microprocessor in the appliance. Also, the devices illustrated in the last-mentioned figures may be retained securely engaged in the nesting site of the appliance, or in contact with one another, as the case may be, in various ways including, by way of example, a clamp (not shown) mounted on the appliance, binding of the confronting device surfaces to one another, e.g., by adhesive, or by appropriate dimensioning the devices relative to the nesting sites to frictionally retain the devices therein.

Figure 8A:
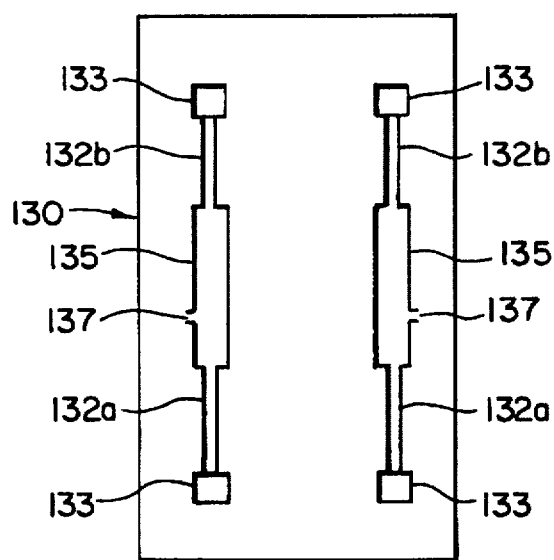
FIGS. 8A and 8B show, in plan view, diagrammatic illustrations of two analytical devices intended for use with the sample preparation device of the invention. The device of FIG. 8A has two mesoscale flow systems, each one including inlet ports interconnected by a flow channel to a single chamber for analyte capture and, optionally, detection.

A biological assay device which may be used in combination with the sample preparation device of the invention is shown in FIG. 8A. The device 130 was fabricated on a substrate 131 having mesoscale flow channels 132a, 132b with entry ports 133 microfabricated on opposite ends of the channels and a central mesoscale mixing/capture/detection chamber 135. As depicted in FIG. 8A, the cross-sectional dimension of chamber 135 is relatively larger than that of channel 132a, 132b.

A capture reagent, such as a substance that binds specifically to the analyte of interest, may be immobilized, either on a stationary or mobile support, in chamber 135. When a mobile support, e.g. polymer particles, is used, the particle size should be selected so as to be relatively larger than the cross-sectional dimension of flow channel 132a, 132b in order that the immobilized reagent is confined to chamber 135. A reagent immobilized on a particulate solid support in this manner can conveniently be charged to chamber 135 via inlet port 137.

A device of the type just described can be used to carry out various immunoassay reactions. For example, a non-competitive, immunometric assay for the determination of carcinoembryonic antigen (CEA) may be carried out by filling chamber 135 with monoclonal anti-CEA antibodies immobilized on a particulate support, such as plastic beads. The test sample to be analyzed for CEA is then added to fill chamber 135 and expel any fluid introduced with the immobilized reagent. The contents of chamber 135 are thereafter incubated for a time sufficient to effect antigen-antibody binding. Subsequently, an antibody enzyme conjugate, e.g. monoclonal anti-CEA antibody-horseradish peroxidase is added to the chamber and the contents are again incubated. A solution of a chromogenic substrate is then added to chamber 135 which serves to wash the immobilized reagent, expelling unbound conjugate. Sufficient substrate is retained in the chamber to react with any peroxidase label bound to the immobilized reagent. The rate of generation of chromophore is directly proportional to the concentration of CEA in the sample.

Device 130 may also be used to perform a competitive assay for the determination of thyroxine in a test sample. In carrying out this format, chamber 135 is filled with an immobilized reagent comprising anti-thyroxine antibodies bound to the surface of plastic beads. The test sample to be analyzed for thyroxine is premixed with a thyroxine-peroxidase conjugate and added to the chamber, thus filling the chamber and expelling any fluid introduced with the immobilized reagent. The contents of the chamber are then incubated for a time sufficient to effect antigen-antibody binding. A buffer may optionally be passed through chamber 135 to wash the immobilized reagent. A chromogenic substrate is thereafter added to the chamber, washing the immobilized reagent and expelling any unbound reagents. Sufficient substrate is retained in chamber 135 to react with any peroxidase label bound to the immobilized reagent. Generation of chromophore is inversely proportional to the concentration of thyroxine in the test sample.

Although the assay structure of FIG. 8A is configured to confine the immobilized reagent in channel 135, the design is such that fluid can be pumped over and through the immobilized reagent for washing purposes.

It should be understood that the last-mentioned two examples are merely representative, as the device of FIG. 8A, as well as the other devices described herein may be used to implement a variety of other assay formats.

Figure 8B:
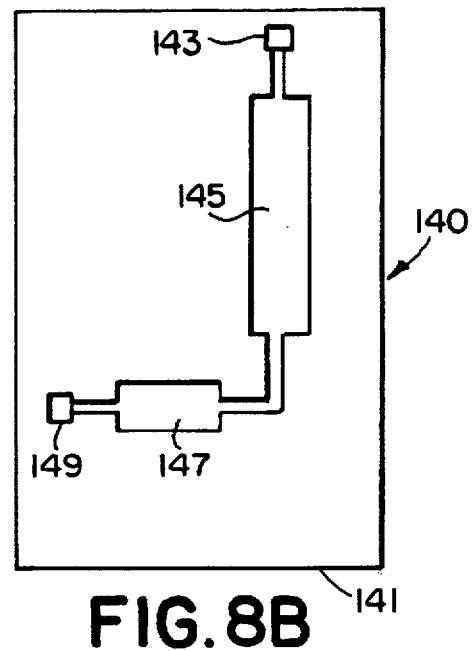

FIG. 8B shows analytical device 140 microfabricated on a substrate 141 and having an inlet port 143 in fluid communication with a chamber 145 for analyte capture, e.g., by immunocapture. This device is adapted for carrying out enzyme immunoassay. To that end, the device includes a separate chamber 147 containing a binding agent to capture and concentrate the chromophore produced by the action of the enzyme label on a suitable substrate. For example, a protein analyte may be determined using a "sandwich" assay technique, in which the analyte is captured in chamber 145 by an antibody immobilized therein which binds specifically to the analyte. The captured analyte is labelled with an enzyme-antibody conjugate composed of alkaline phosphatase, for example, and an antibody that specifically binds the protein analyte. Fluorescein phosphate is introduced into chamber 145 as a chromogenic substrate for the enzyme label. Alkaline phosphatase acts on the substrate to generate fluorescein which is captured by an anti-fluorescein antibody immobilized in chamber 147. A hydrophobic environment created in chamber 147, e.g., by virtue of material adhered to the walls of the structure, the capture agent or a component of the reaction mixture, e.g., a surfactant or micelle-forming agent, will improve the fluorescent signal from the bound fluorescein. Detection of the chromophore may be carried out in chamber 147 or the chromophore may be removed from the device through outlet 149 for detection in a separate apparatus. Other substrates could be selected for use in carrying out this determination, such as 4-nitrophenol phosphate or 4-methylumbelliferone phosphate, with appropriate binding agents used to capture the dephosphorylated product.

Figure 9:
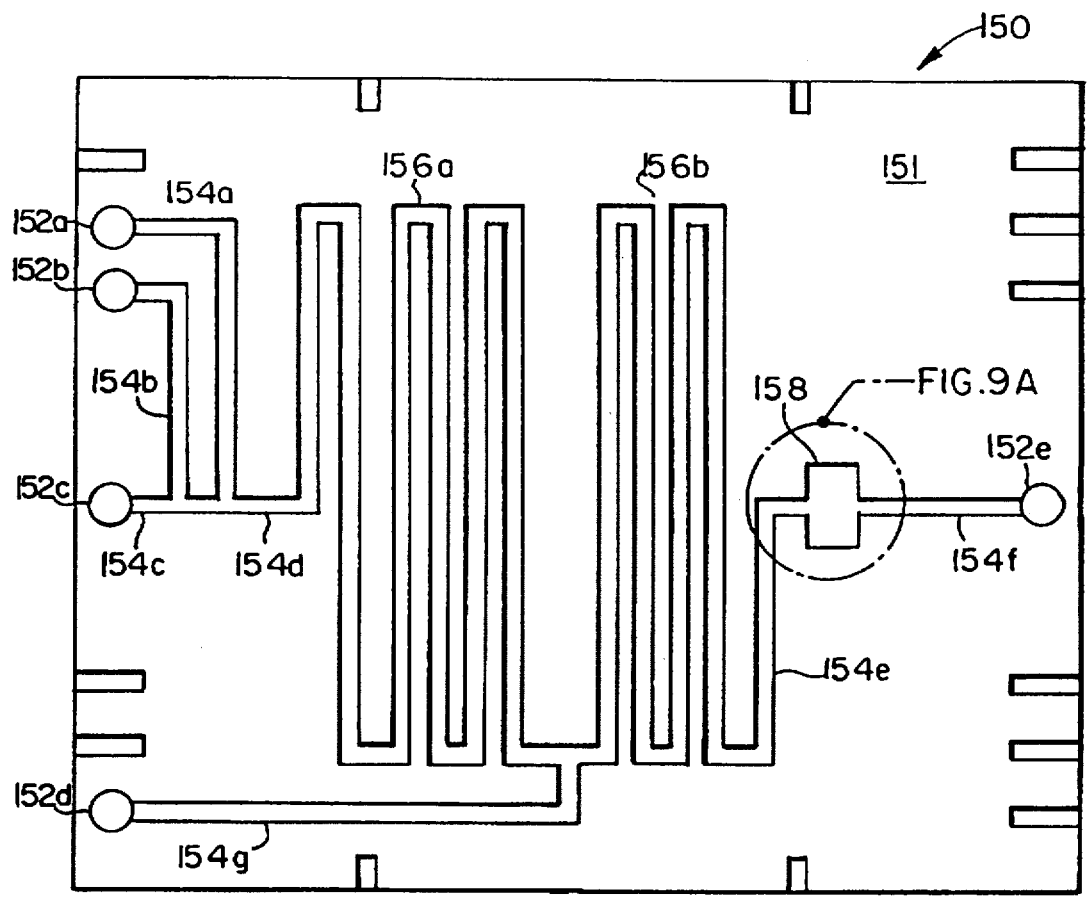
FIG. 9 is a plan view of a diagrammatic representation of a microfabricated analytical device intended for use with the sample preparation device of the invention. The analytical device includes a set of tortuous channels which enable the timed addition and mixing of reagents, wash liquids and the like used in conducting various assay protocols.

A diagrammatic representation of another embodiment of a biological assay device that may be used in the practice of the present invention is shown in FIG. 9. The substrate 151 of device 150 is microfabricated with ports 152a–e, flow channels 154a–g, reaction chambers 156a and 156b and a capture/detection chamber 158. The reaction chambers 156a and 156b each comprise a tortuous mesoscale flow channel. The path length of the tortuous channel may be designed to permit the timed mixing and addition of sample reagent(s). Devices of this type may be utilized in combination with an appliance having ports mated to ports in the device, which appliance is capable of delivering and receiving fluids through the flow system of the device and, optionally, capable of optically detecting a positive or quantitative result in chamber 158. In one application of the device, the cholesterol content of a sample may be determined. Cholesterol esterase is applied via inlet port 152a and buffer and sample are added via inlet ports 152b and 152c, respectively. The mixture then flows through channel 154d to the tortuous mixing/reaction chamber 156a. The time of mixing and reaction may be predetermined by microfabricating the tortuous channel to the appropriate length and controlling the flow rates. Cholesterol oxidase is added via port 152d and flows through channel 154g to the tortuous channel 156b where the timed mixing and reaction of the cholesterol oxidase with the fluid from channel 156a occurs. Heating means like those described above, may be provided to maintain the device at 37° C., or higher. A chromogenic substance is introduced at 154e through a flow channel (not shown) for detection. Positive or quantitative results can be detected optically by observing the detection chamber 158, e.g., through an optical window disposed over the chamber. The detection chamber 158 may be provided with an immobilized binding moiety capable of capturing the product of the enzyme reaction, thus facilitating detection. This device may be applied to a range of clinical enzymatic and other reactions.

Figure 9B:
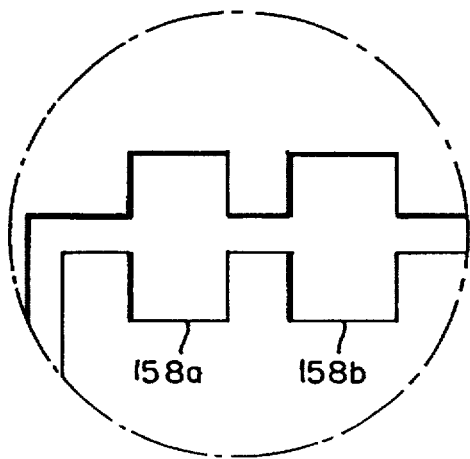
FIG. 9B shows an exploded view of a part of an alternative embodiment of the device having an analyte capture chamber and a separate analyte detection chamber.

According to an alternative embodiment shown in FIG. 9B, capture of a fluorescently labelled analyte may occur in chamber 158a, which contains an analyte-specific binding agent that binds releasably to the analyte. Released fluorescently labelled analyte is captured for detection in chamber 158b.

Figure 9C:
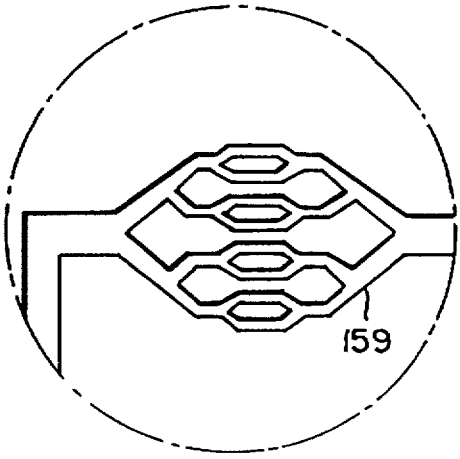
FIG. 9C shows an exploded view of part of another embodiment of the device including a branched flow passage region which permits analyte detection based on flow restriction in the branched region.

In another embodiment illustrated in FIG. 9C, flow channel 154f may be constricted, such that the flow passage is of smaller cross-sectional area than channel 154e, thereby restricting flow of test fluid through the device. As depicted in FIG. 9C, channel 154f is constructed in a pattern of parallel flow channels, with reduced dimensions at each channel division, providing sequentially narrower flow passages. This device may be utilized in performing various agglutination assays, the occurrence of particle-induced or complex-induced agglutination being detected on the basis of restricted flow of the sample through the branched portion 159 of flow channel 154f.

Figure 10A:
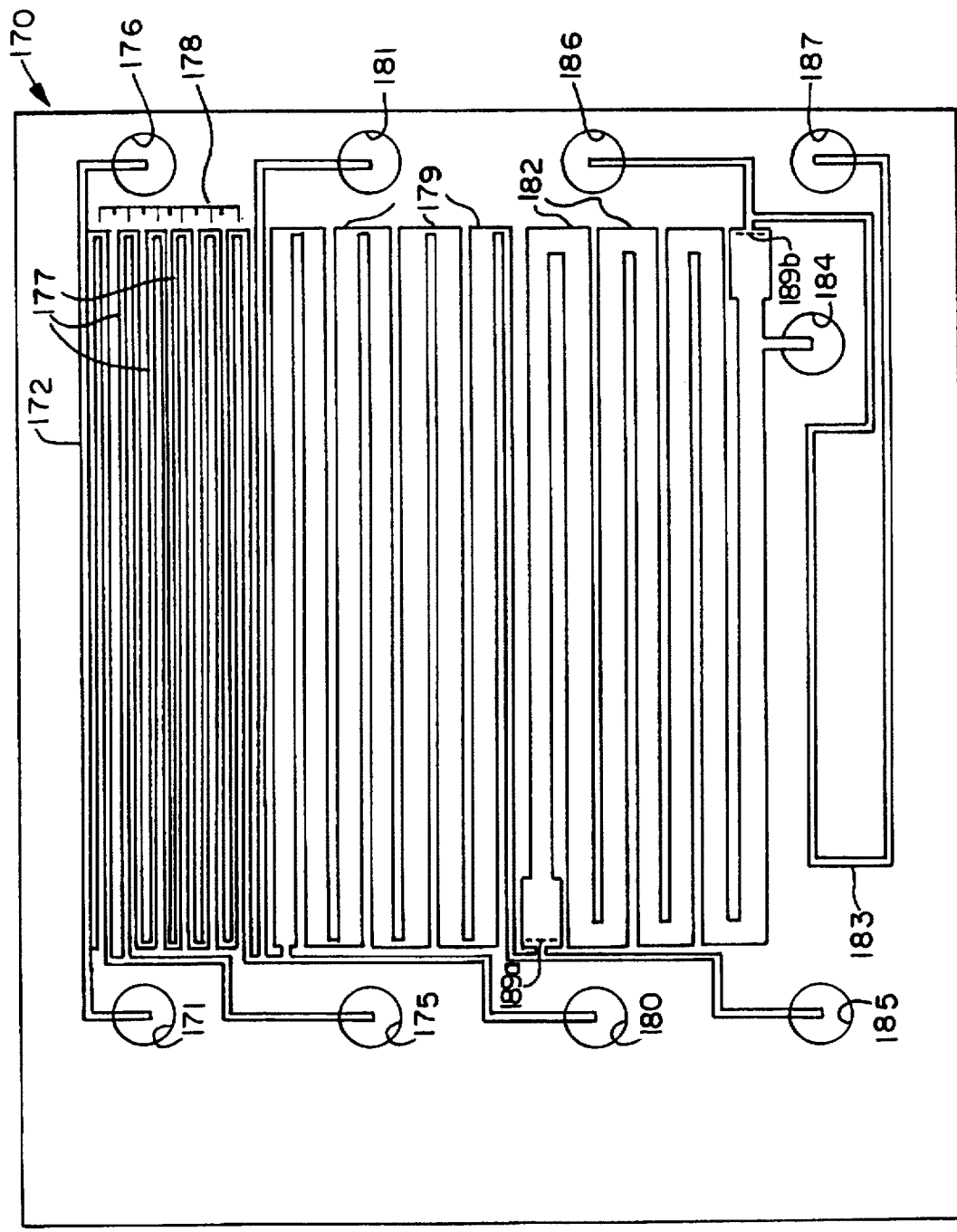
FIG. 10A is a plan view of a diagrammatic representation of another embodiment of an analytical device for carrying out various assay protocols on microvolume samples, which may be used together with the sample preparation device of the present invention.

FIG. 10A is a diagrammatic representation of a mesoscale analytical device 170 design for carrying out various binding assay protocols. The device enables determination of a range of analytes on the basis of microvolumes of sample and small, measured amounts of reagents, with labelled product being detected within the device, so that all sample, unreacted reagent and reaction products remain confined in the device for subsequent disposal.

The device may be used in combination with an appliance (not shown) of the general type described above with reference to FIG. 6A. Such a device has a nesting site for holding the device, flow lines and associated pumps and valves for delivering sample, reagents, wash solutions and the like to the device. The appliance may also include a temperature control and sensing means, pressure sensors and/or electrical connections to facilitate analyte detection, optical detection means, signal amplification and quantitation means, all as described herein. The combination may also include overall system sequence and control elements, quantitated information display and recording means via a microprocessor in the appliance, for example, or by interfacing with an external computer.

The device is microfabricated as previously described with the flow passages configured to provide a total capacity in the range of 0.01–100 µL, preferably from about 0.5 to about 50 µL.

Figure 10B:
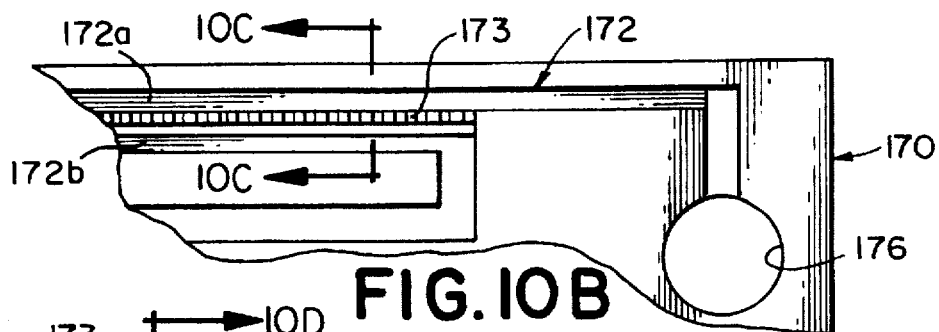
FIG. 10B is an exploded fragmentary plan view of a part of the first flow passage through which sample fluid flows upon its introduction into the sample inlet port of the device shown in FIG. 10A.
Figure 10C:
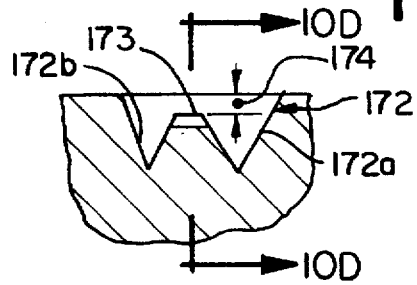
FIG. 10C is a fragmentary transverse cross-section of the first flow passage taken along the line 10C—10C in FIG. 10B, showing the side-by-side v-shape channels which constitute the first flow passage.
Figure 10D:
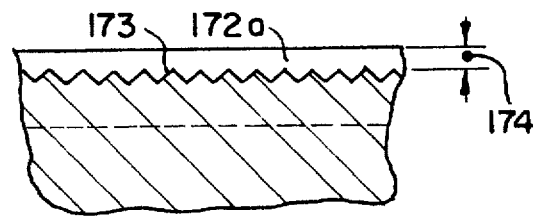
FIG. 10D is a fragmentary longitudinal cross-section of the first flow passage taken along the line 10D—10D in FIG. 10C, showing certain structural features of the barrier separating the v-shaped channels.

In use, a microvolume of test sample fluid is introduced at port 171. The test sample fluid may be pre-filtered, e.g., by passage through the sample preparation device of the invention, before introduction at port 171. Alternatively, the sample fluid may be filtered after introduction into device 170. Internal filtration may be beneficially achieved by a cross-flow filtration technique. As shown in FIG. 10B, flow passage 172, through which sample fluid initially passes upon introduction at inlet 171, is divided into two side-by-side V-shaped channels 172a and 172b, separated by a longitudinal barrier 173, which is preferably formed from the substrate material (but may be a part of, and suspended from the cover plate or sheet). Barrier 173, together with the cover of the device, defines at least one passageway 174, as illustrated in FIG. 10C, which allows fluid flow therethrough, but is of sufficiently small dimension to prevent the passage of particulate components, e.g., cells, of a fluid sample. Barrier 173 is positioned such that inlet 171 feeds sample fluid directly into flow passage 172a and indirectly into flow passage 172b, the fluid passing into flow passage 172b having a substantially reduced particle content, as compared with previously unfiltered sample entering inlet 171.

Flow passage 172 may be fabricated with walls that diverge from a relatively small cross-sectional dimension to a relatively larger cross-sectional dimension in the downstream direction from the inlet, or with walls that converge from a relatively large cross-sectional dimension to a relatively smaller cross-section dimension in the downstream direction from the inlet, with barrier 173 being disposed generally parallel to at least one of the passage walls. Such design gives rise to nonlinear flow of the sample fluid which aids in dislodging particles from passageway 174.

If the test sample fluid is filtered externally to device 170, the above-described internal filter may be omitted. Alternatively, a sample fluid that has been externally filtered can be entered directly into the device via port 175, thus bypassing flow passage 172. A buffer may also be introduced through port 175 for the preparation of diluted sample fluid, if desired. Excess buffer may be collected in outlet 176.

Particulate matter trapped in flow passage 172a is conveyed to outlet 176, as illustrated in FIG. 10B.

Filtrate from flow passage 172b next passes into flow passage 177 which is appropriately dimensioned to function as a metering chamber, providing a pre-determined sample volume for analysis. The pre-determined sample volume will ordinarily be on the order of about 1 µL. A scale 178 may be provided on device 170, e.g., by etching, to aid in the metering of desired amounts of sample fluid into the device for analysis. By enabling the introduction of prescribed sample volumes into device 170, flow passage 177 also permits quantitation of the analyte.

A suitable impellent (not shown) incorporated in device 170, or in an appliance designed for use in conjunction with such device, can be employed for transferring the metered sample fluid to flow passage 179, which is optionally provided for mixing the sample fluid with the primary reagent used in performing the binding assay. The inclusion of such a mixing chamber in device 170 is beneficial for achieving more rapid and complete reaction between analyte and primary reagents.

Suitable impellents for transferring sample fluid, reagents, buffers and the like through the flow system of device 170 includes various pumps, such as micromachined pumps, diaphram pumps, syringe pumps, volume occlusion pumps, as well as endosmotic induced flow, flow induced by electrochemical evolution of gases and other pumping means known to those skilled in the art.

The primary reagents may be delivered directly to flow passage 179 in the device through inlet 180. The primary reagents are caused to mix with the metered sample fluid upon entering flow passage 179, which may be sequential or essentially simultaneous. Excess primary reagents may pass out of the flow system through outlet 181.

The source of primary reagent may be an internal storage chamber which can optionally be provided in device 170. Alternatively, the primary reagents can be delivered to the device from a reservoir in an appliance with which the assay device is used, such as the appliance described with reference to FIG. 6A, above, or from some other source external to the device. The primary reagents can be stored as liquid solutions, gels or neat, such as in dried or lyophilized form, or in any other convenient form. For example, the primary reagent can be lyophilized in place in flow passage 179, in which case the test sample fluid or a suitable solvent introduced, for example, through inlet 180 can be used to dissolve the primary reagents. Alternatively, the test sample or a solvent may be directed by liquid transfer means, as noted above, from flow channel 179 to a storage chamber (not shown) outside the flow system illustrated in FIG. 10 to dissolve the primary reagents. In addition, heating or agitation means (not shown) may be provided in the storage chamber to aid in dissolving the primary reagents stored therein.

The primary reaction mixture, comprising the sample fluid and dissolved primary reagents can also be reacted in flow channel 179, which may include structural elements, as previously described, to promote turbulent flow. Agitation or other means may be provided to ensure adequate mixing of the primary reaction mixture. The primary reaction mixture is caused to remain in flow channel 179 for a time sufficient for the desired reaction to proceed to completion.

Means for regulating the temperature in flow channel 179, such as that previously described with reference to FIG. 7, may optionally be utilized to enhance the primary reaction conditions. Means for sensing the temperature in flow passage 179 may also be provided, if desired. The temperature sensing means may be operatively connected to a microprocessor or similar device which controls the overall function of the system so as to correlate the sensed temperature with the residence time of the primary reaction mixture in flow passage 179.

Upon completion of reaction, all or part of the primary reaction mixture can be transferred, e.g., by the above-described pumps or other impellents, to capture region 182 and detection region 183, in which one or more original components of the sample fluid or products of the primary reaction may be monitored and/or detected. Alternatively, the product of a secondary reaction, the existence or concentration of which is correlatable to the existence or concentration of the analyte of interest in the sample fluid, can be employed for analyte determination.

The detection techniques utilized in connection with device 170 are those customarily used in performing binding assays. Briefly, these include chemical tests, such as may be carried out by addition of test reagents; spectroscopy, for example, to detect changes in properties of the analyte caused by chemical changes during the primary reaction, such as shifts in absorbance, wave lengths, changes in fluorescence polarization, changes in fluorescence stokes shifts, and the like; agglutination, as measured by microscope, image analysis or similar procedures; and measuring electrochemical performance of the reacted primary reaction mixture, such as specific measurement by amperometric and/or potentiometric/voltametric techniques.

With regard to carrying out a secondary reaction for analyte determination, a capture region, defined by flow passage 182, is provided into which all or part of the reacted primary reaction mixture is transferred by liquid transfer means of the type previously described, and in which one or more components of the products in the primary reaction mixture may be captured by binding to a surface and subsequently detected and/or quantitated. Capture reagent may be immobilized on the walls of flow passage 182 or on the surface of particles or beads present in flow passage 182, or both.

An inlet or fill hole 184 may be provided to pre-fill flow passage 182 with solid phase capture reagent comprising plastic, latex, silica or other suitable support material, including magnetic components, capable of combining specifically to the products of the primary reaction mixture. The particulate capture reagent can be charged to flow passage 182 either as a wet slurry, which may subsequently be dried or lyophilized, or in dry form. In either case, the filling of flow passage 182 can optionally be assisted by vibration or other means. The mobile solid phase of the capture reagent comprises particles or beads having diameters from tens of nanometers to tens of microns, with a surface coating of avidin, strepavidin or other substance to which biotinylated or otherwise conjugated antibodies will specifically bind.

Flow passage 182 may be fabricated with flow restricting structural elements 189a, 189b or other means to confine the capture reagent within flow passage 182 while allowing passage of fluids therethrough. The particulate capture reagent may also be confined within flow passage 182 in the manner previously described with reference to FIG. 8A.

The primary reaction mixture is caused to remain in flow passage 182 for a time sufficient for reaction with the capture reagent to proceed to a known extent, preferably essentially to completion. Means for regulating and sensing the temperature in flow passage 182 may optionally be provided as noted above with reference to flow passage 179.

The captured product of the primary reaction mixture is preferably washed before proceeding with the secondary reaction.

The reagent solution for the secondary reaction may be delivered directly to device 170 via inlet 185. Excess secondary reagent may be removed from the flow system through outlet 186 or 187. Alternatively, the reagent for the secondary reaction may be kept prior to dissolution and use in a storage chamber in device 170, or in an appliance used in conjunction with the device, or in some other convenient source external to the device. One or more flow lines appropriately mated with flow passages in device 170 and operatively connected to an impellent may optionally be provided to transfer solvent from an input port to the above-mentioned secondary storage chamber where stored reagents are dissolved to form the secondary reaction solution.

The reagent for the secondary reaction may include an enzyme substrate specific to an enzyme conjugated to the captured primary reaction product, as well as substances which, when dissolved in the secondary reaction solution, assist in washing of the bound primary reaction product.

The secondary reaction preferably occurs in flow passage 182, wherein the secondary reaction solution reacts with captured primary reaction products. The product of the secondary reaction may be a substance selected from the group of molecules or ions directly or indirectly detectable based on light absorbance, fluorescence, phosphorescence properties; molecules or ions detectable by their radioactive properties; or molecules or ions detectable by their nuclear magnetic resonance or paramagnetic properties. The product of the secondary reaction may be amplified, according to procedures known in the art to enhance the detection thereof. For example, an enzyme amplification reaction may be employed, which releases a florophore generated from a non-fluorescent precursor in the secondary reaction solution.

After the secondary reaction is complete, the resultant product may be detected and quantitated either within flow passage 182 or subsequently in detection region 183, or in a detector external to device 170.

The preferred cross-sectional dimensions of flow passages 177 and 183, transverse to the path of flow of sample fluid, are about 100 μm wide and 70 μm deep, whereas the preferred cross-sectional dimensions of flow passages 179 and 182, transverse to the path of flow of sample fluid, are about 400 μm wide and 70 μm deep. These dimensions are within the mesoscale range, as set forth above.

Various binding assay protocols can be implemented in device 170 including immunometric (sandwich) assays as well as competitive immunoassays, employing both polyclonal and monoclonal antibodies for purposes of capture and detection of analyte. One form of detection antibody comprises a conjugated label wherein the label is florophore detectable as a bound moiety after capture on a solid phase. Another form of detection antibody comprises a conjugated label wherein the label is florophore detected after release from the captured primary reaction product. Another form of detection antibody comprises a conjugated enzyme moiety such as horseradish peroxidase or alkaline phosphatase.

Washing steps may be carried out as appropriate to eliminate potentially interfering substances from device 170.

Excess sample fluid, reagents, wash solutions and the like from the various flow passages and structural elements may be combined and routed into a single waste receptacle of adequate capacity, preferably within device 170, such that all sample fluid and reaction products are safely contained for disposal.

Figure 11A:
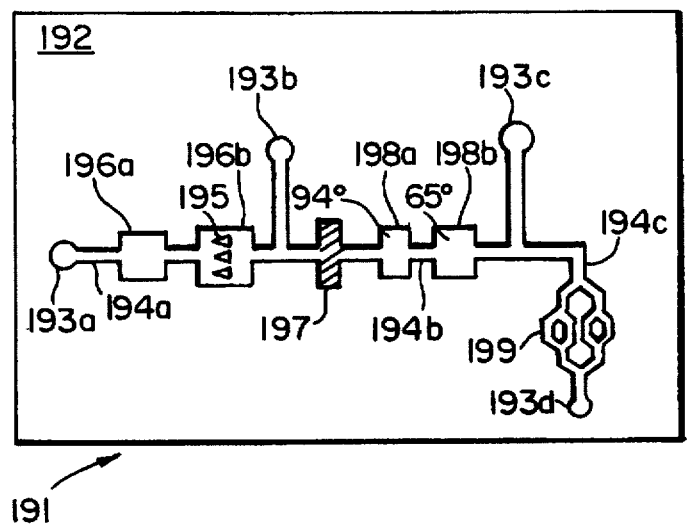
FIG. 11A is a plan view of a diagrammatic representation of an analytical device intended for use with the sample preparation device of the invention, the analytical device having a series of mesoscale chambers suitable for implementing a variety of procedures including cell sorting, cell lysing and polynucleotide amplification, e.g., PCR.

FIG. 11A diagrammatically depicts an analytical device 191 used to determine the presence of an intracellular polynucleotide in a biological cell-containing fluid sample, and then to perform an assay for a particular nucleotide sequence. Microfabricated on substrate 192 is a mesoscale flow passage 194a–c which includes a cell separation chamber 196a, a cell lysis chamber 196b, a filter element 197, a polynucleotide amplification chamber comprising sections 198a and 198b, and a detection region 199. The mesoscale flow system is also provided with fluid entry/exit ports 193a–d. The device can be used in combination with an appliance, such as that described above with reference to FIG. 6A.

Initially, the valves in the above-mentioned appliance function to close ports 193c and 193d, while ports 193a and 193b are open. A sample containing a mixture of cells, e.g., transferred from the sample preparation device, is directed to the sample inlet port 193a by a suitable impellent, e.g. a pump, (not shown), and flows through the mesoscale flow channel 194a to separation chamber 196a. Chamber 196a contains binding moieties immobilized on the wall of the chamber which selectively bind to a surface molecule on a desired cell type in the sample. Remaining cellular components exit the substrate via port 193b. After binding of the desired cell type in chamber 196a, flow with buffer is continued, to wash and assure isolation of the target cells. Next port 193b is closed and 193c is opened. Flow is then increased sufficiently to dislodge the immobilized cells from chamber 196a. Flow is continued, forcing cells through membrane piercing protrusions 195 in chamber 196b, which tear open the cells releasing intracellular material.

Sample flow continues past filter 197, which filters off large cellular membrane components and other debris, with the filtrate passing to mesoscale PCR chamber section 198a, which is connected to PCR chamber section 198b by flow channel 194b. Taq polymerase, primers and other reagents required for the PCR assay next are added to section 198b through port 193c from a source thereof (not shown), permitting mixing of the intracellular soluble components from the separated subpopulation of cells and the PCR reagents. With the ports closed (to ensure that the reaction mixture does not evaporate, or otherwise becomes lost from the device), an impellent, e.g. a pump, (not shown), applies a motive force to port 193b to cycle the PCR sample and reagents through flow channel 194b between sections 198a and 198b, set at 94° C. and 65° C., respectively, to implement plural polynucleotide melting and polymerization cycles, allowing the amplification of the polynucleotide of interest. Before the next process step, port 193c is closed and port 193d is opened. The same impellent force is then used to direct the amplified polynucleotide isolated from the cell population to a detection region 199 in the form of a pattern of flow channels like that described above with reference to FIG. 9C. Flow reduction in the restricted region serves as a positive indicator of the presence of amplified polynucleotide product and may be detected optically through a glass cover disposed over the detection region 199.

Alternatively, the amplified polynucleotide product may be detected directly in the reaction chamber, using commercially available reagents developed for such purpose, such as the "Taq Man®" reagents, available from Perkin Elmer Corporation. The amplified polynucleotide may also be detected outside the device using various methods known in the art, such as electrophoresis in agarose gel in the presence of ethidium bromide.

Figure 11B:
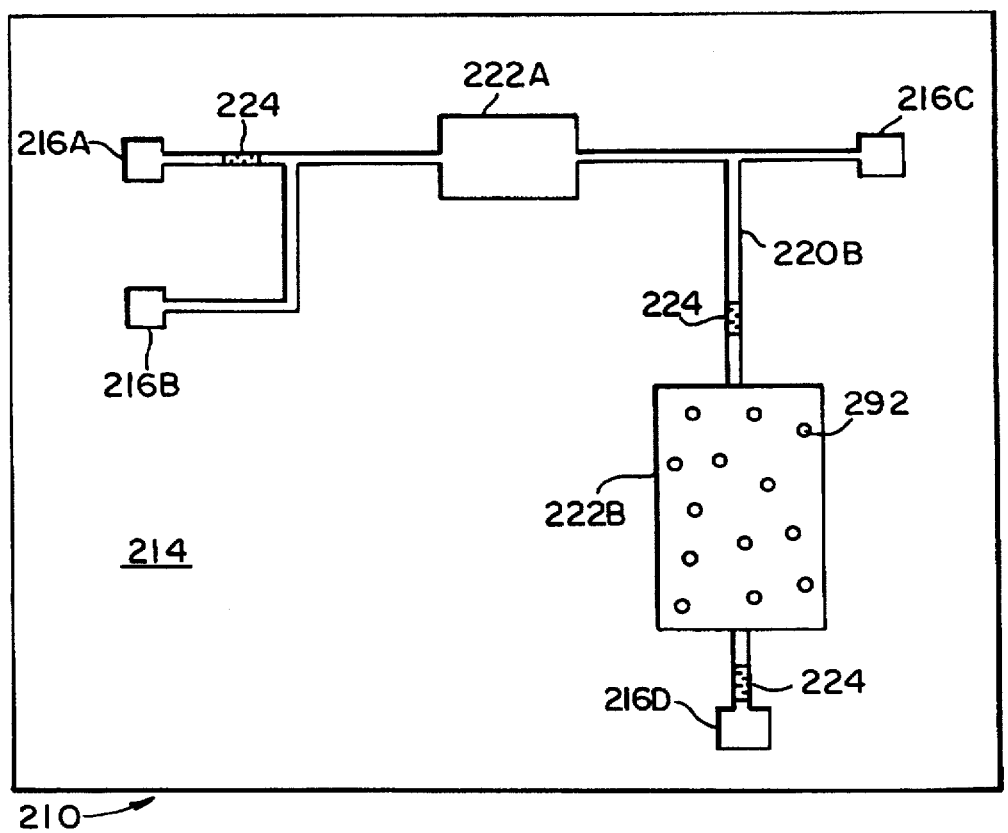
FIG. 11B is a plan view of a diagrammatic illustration of an alternative design for a mesoscale PCR analytical device.

Another embodiment of an analytical device which is useful in the practice of this invention is illustrated in FIG. 11B. The device 210 comprises a substrate 214 microfabricated with a mesoscale polynucleotide amplification chamber 222A. The device 210 can be used in combination with an appliance like appliance 90 shown in FIG. 7. The appliance is provided with flow passages mated to ports 216A, 216B, 216C and 216D in device 210. The appliance may also include valves that allow the ports 216A, 216B, 216C and 216D to be mechanically opened and closed. In one embodiment, the flow system of the devices may be maintained at a hydraulically full volume, and valves in the appliance, or alternatively, in the devices themselves, may be utilized to direct fluid flow. Chamber 222A is heated and cooled to temperatures appropriate to provide a dehybridization temperature, and annealing and polymerization temperatures, as required for PCR. Temperature of the reaction region can be controlled as previously described with reference to FIG. 7.

The flow system illustrated in FIG. 11B includes filter elements 224, of the general type described herein, to remove from the sample fluid filterable components having a tendency to interfere with the analysis.

In operation, a sample containing polymerase enzyme and other reagents required for PCR is delivered through inlet port 216A to reaction chamber 222A. With the ports closed, a heating element is then utilized to thermally cycle the reaction chamber between a temperature suitable for dehybridization and temperatures suitable for annealing and polymerization. When the PCR reaction cycle is terminated, ports 216B and 216D are opened, driving the contents of chamber 222A to detection region 222B, which region contains a polynucleotide probe, e.g., immobilized upon beads 292. A positive assay for the polynucleotide is indicated by agglutination of the beads in the detection region.

Although polynucleotide amplification has been described herein with particular reference to PCR, it will be appreciated by those skilled in the art that the devices and systems of the present invention may be utilized equally effectively for a variety of other polynucleotide amplification reactions. Such additional reactions may be thermally dependent, such as the polymerase chain reaction, or they may be carried out at a single temperature (e.g., nucleic acid sequenced-based amplification (NASBA)). Moreover, such reactions may employ a wide variety of amplification reagents and enzymes, including DNA ligase, T7 RNA polymerase and/or reverse transcriptase, among others. Additionally, denaturation of polynucleotides can be accomplished by known chemical or physical methods, alone or combined with temperature change. Polynucleotide amplification reactions that may be practiced in the device of the invention include, but are not limited to: (1) target polynucleotide amplification methods such as self-sustained sequence replication (3SR) and strand-displacement amplification (SDA); (2) methods based on amplification of a signal attached to the target polynucleotide, such as "branched chain" DNA amplification (Chiron Corp., Emeryville, Calif.); (3) methods based on amplification or probe DNA, such as ligase chain reaction (LCR) and QB replicase amplification (QBR); (4) transcription-based methods, such ligation activated transcription (NASBA); and (5) various other amplification methods, such as repair chain reaction (RCR) and cycling probe reaction (CPR) (for a summary of these methods and their commercial sources, see pp. 2–7 of *The Genesis Report*, DX, Vol. 3, No. 4, February 1994; Genesis Group, Montclair, N.J.).

The sample preparation device of the invention may be used in conjunction with Mesoscale Polynucleotide Amplification Devices, which is the subject matter of U.S. Ser. No. 08/308,199, now U.S. Pat. No. 5,498,392 (Attorney Docket No. G 1158), which is being filed contemporaneously with the present application. The entire disclosure of the last-mentioned application is incorporated by reference herein.

Briefly, the last-mentioned patent application relates to mesoscale devices for amplification of a preselected polynucleotide in a sample fluid. The devices are provided with a substrate microfabricated to include a polynucleotide amplification reaction chamber having at least one cross-sectional dimension of about 0.1 to 1000 µm. The device also includes at least one port in fluid communication with the reaction chamber, for introducing a sample to the chamber, for venting the chamber when necessary, and, optionally, for removing products or waste material from the device. The reaction chamber may be provided with reagents required for amplification of a preselected polynucleotide. The device also may include means for thermally regulating the contents of the reaction chamber, to amplify a preselected polynucleotide. Preferably, the reaction chamber is fabricated with a high surface to volume ratio, to facilitate thermal regulation. The amplification reaction chamber also may contain a composition which diminishes inhibition of the amplification reaction by material comprising a wall of the reaction chamber, when such treatment is required.

Appliances 30, 50, 70 and 90, as shown in FIGS. 4, 6A, 6B and 7, respectively, may also be utilized to deliver metered amounts of sample, reagent buffer and the like, as well as to implement the timed addition of sample or other fluids to the devices in connection with the performance of prescribed analytical protocols.

In those cases where a microprocessor is included in the appliance it may be used to assist in the collection of data for one or a series of analyses.

Although analyte determination has been described above with particular reference to whole blood as the sample fluid, the analyte of interest may be present in test samples or specimens of varying origin, including other biological fluids such as whole blood containing anti-coagulants, dilute whole blood, lysed whole blood, whole blood containing assay reagents, serum, plasma, urine, sperm, cerebrospinal fluid, amniotic fluid, lavage fluids, tissue extracts, cell suspensions and any other sample fluid that can be beneficially analyzed using the device and systems described herein.

Figure 12A:
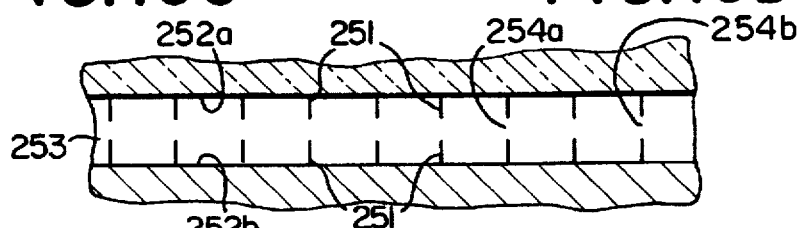
FIGS. 12A and 12B are fragmentary plan views of additional embodiments of microfabricated, restricted flow separators disposed in the flow passage of a sample preparation device of the invention.
Figure 12B:
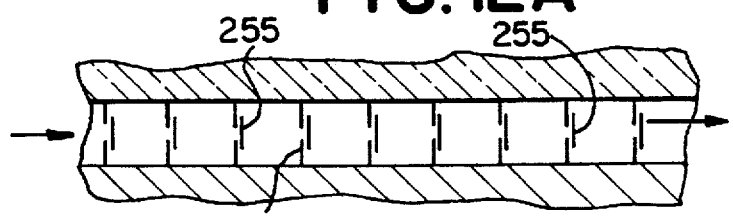

FIGS. 12A–D illustrate various additional embodiments of microfabricated, restricted flow separators which may be disposed in the flow passages of the devices described herein. The separator in FIG. 12A is in the form of a plurality of partitions 251, projecting from opposite surfaces 252a, 252b of channel 253, so as to define a series of passageways 254a, 254b, which are aligned longitudinally along the channel. One or more intermediate partitions 255, projecting from the bottom of channel 250 may be disposed adjacent the downstream-facing portion of one or more of partitions 251, to stand as barriers or baffles within the flow passage provided by aligned passageways 253.

Sample fluid passing through the relatively narrow passageways 254a, 254b at relatively high speed will tend to disperse into the space between consecutive partitions, while reducing in speed and moving into the dead volume corners of such space. When sample fluid then passes into the next successive inter-partition space, particulate matter may be relatively retained in the dead volume. Thus, for each passage into a subsequent inter-partition space, particulate matter is progressively retained and sample fluid becomes gradually more purified as it flows downstream through the partitions. With a sufficient number of partitions in series, progressive reduction in particle concentration would be enabled, the efficiency of which could be predetermined. Baffles 255 would assist in directing the sample fluid into the dead volume region.

Figure 12C:
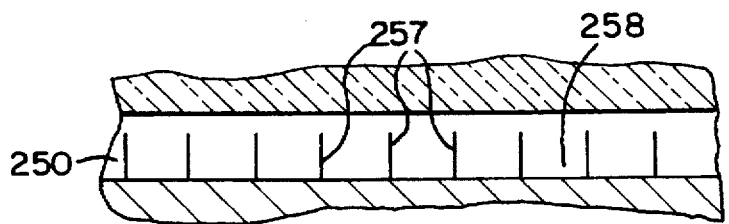
FIGS. 12C and 12D are fragmentary longitudinal sectional views of other additional embodiments of microfabricated restricted flow separators disposed in the flow passage of the sample preparation device of the invention.

In FIG. 12C, there is shown a weir-type separator structure formed by barriers 257 projecting up from the bottom 258 of channel 250.

Figure 12D:
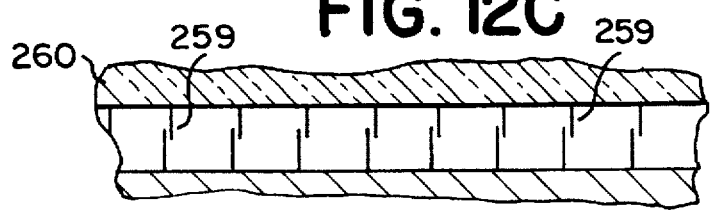

The separator structure shown in FIGS. 12C and 12D takes advantage of the propensity of particles to fall under the influence of gravity. This may be particularly useful in the analysis of whole blood, by promoting the sedimentation of erythrocytes. The sample fluid passes at high speed over barrier 257, then immediately slows. Any particulate matter falling towards the floor of channel 250 will experience a lower supporting velocity and a diminished opportunity of being swirled up over the next succeeding barrier. Passage of sample fluid over a series of such barriers may progressively reduce particulate concentration and produce gradually more purified sample fluid. One or more lips 259 suspended from cover plate 260 assists in downwardly directing the sample fluid.

The following examples are provided to describe the invention in further detail. These examples are intended to illustrate and not to limit the invention.

EXAMPLE 1

A plastic-silicon composite assay device was fabricated by attaching a plastic (3M transparency sheet) cover over a silicon substrate 131, microfabricated with flow channels 132a, 132b having entry ports 133 on opposite sides of the channel and a central reaction/detection chamber 135, as shown schematically in FIG. 8A. A dilution of anti-A (in 0.05M sodium bicarbonate pH 9.6) and a 1:10 dilution of Type A blood in saline were introduced via syringe using a holder into the entry ports 133 on opposite ends of the channel 132a, 132b. The solutions mixed together in the central chamber 135 and agglutination was observed through the plastic cover by light microscopy. The results are summarized in the following table.

| ANTI-A | DILUTION | AGGLUTINATION IN CHANNEL |
|---|---|---|
| Gamma Kit | 1:20 | + |
| Gamma Murine Mono | 1:20 | + |
| Gamma Human Dilution | 1:5 | + |
| Immucor Affinity pure | 1:100 | + |
| Immucor Ascites | 1:100 | + |

EXAMPLE 2

A solution of mouse IgG (50 µg/mL in 0.05M sodium bicarbonate pH 9.6) (SIGMA Cat. No. 1-5381) and a 1:20 dilution of goat anti-mouse IgG (H&L)—fluorescence carboxylate beads (Polysciences, Inc.) in PBS buffer were introduced via syringe using a holder into the entry ports on opposite ends of channels 132a, 132b in another assay device prepared as described in Example 1. The solutions were mixed together in the reaction/detection chamber 135 and agglutination was observed through the transparent plastic cover by light microscopy.

While certain embodiments of the present invention have been described and/or exemplified above, various other embodiments will be apparent to those skilled in the art from the foregoing description. The present invention is, therefore, not limited to the particular embodiments described and/or exemplified, but is capable of considerable variation and modification without departure from the scope of the appended claims.

What is claimed is:

1. A device for preparing a test sample, comprising particulate components, for analysis, said device comprising a sample flow passage having a sample inlet and an outlet in fluid communication and a separator disposed between said inlet and said outlet, said separator having an upstream-facing portion defining a separation zone in said flow passage in which said particulate components are collected, and a flow channel in fluid communication with said separation zone for affording discharge of collected particulate components from said separation zone, said channel having an inlet section for directing a carrier fluid into said separation zone and over the upstream-facing portion of said separator, and a discharge section for directing said carrier fluid from over the upstream-facing portion of said separator and out of said separation zone, at least one of said flow passage and said flow channel sections having at least one mesoscale dimension.

2. The device of claim 1, wherein said flow passage has at least one mesoscale dimension and said separator comprises a region of restricted flow in said flow passage, said region of restricted flow being formed by at least one passageway having at least one mesoscale dimension smaller than the least mesoscale dimension of said flow passage and being of a small dimension to separate said particulate components from said test sample.

3. The device of claim 2, wherein said at least one passageway has at least one bend therein such that at least a part of said passageway is generally perpendicular to said flow passage.

4. The device of claim 1, wherein said flow passage and said flow channel are formed in a surface of a solid substrate and enclosed by a cover adhered to said surface.

5. The device of claim 4, wherein said separator is in the form of at least one upstanding projection of said solid substrate which is disposed in said flow passage and which restricts the flow of test sample along said flow passage.

6. The device of claim 4, wherein said cover is transparent.

7. In combination, the device of claim 1 and an appliance for use with said device, said appliance comprising a holder for said device, a test sample input conduit interfitted with the sample inlet of said device and an impellent for moving test sample along said flow passage.

8. The combination of claim 7, wherein said appliance further comprises a reservoir for said test sample.

9. The combination of claim 7, wherein said appliance further comprises a carrier fluid input conduit interfitted with said inlet section of said flow channel and an impellent for moving carrier fluid along said flow channel.

10. The combination of claim 9, wherein said appliance further comprises a reservoir for said carrier fluid.

11. A system for determining an analyte in a fluid sample, said system comprising a sample preparation device, according to claim 1, and an analyte detection device comprising:

a solid substrate fabricated to define:

a sample inlet port; and a flow system comprising:

an analyte detection region in fluid communication with said inlet port, said region containing a reagent which interacts with said analyte to yield a detectable product which is determinative of said analyte, and a detector for detecting said product;

the flow passage outlet of said sample preparation device being in fluid communication with said sample inlet port of said analyte detection device.

12. The system of claim 11, which further comprises, in said analyte detection device, a sample flow channel interconnecting said inlet port and said analyte detection region, at least one of said analyte detection region and said sample flow channel having at least one mesoscale dimension.

13. The system of claim 11, wherein said reagent is a binding substance that binds specifically to said analyte.

14. The system of claim 13, wherein said analyte is an antigen and said binding substance is an antibody.

15. The system of claim 13, wherein said analyte is a ligand and said binding substance is a receptor.

16. The system of claim 13, wherein said analyte is a nucleic acid molecule of predetermined sequence and said binding substance is a nucleic acid molecule having a sequence complementary or homologous to the sequence of said analyte.

17. The system of claim 11 further comprising a device for performing analysis of preselected polynucleotide derived from cells, said analysis comprising a polynucleotide amplification reaction, said polynucleotide analysis device comprising:

a solid substrate fabricated to define:

a sample inlet port; and a flow system comprising:

a polynucleotide amplification region in fluid communication with said inlet port, said polynucleotide amplification region containing reagents for amplifying a polynucleotide, and lysing means intermediate the discharge section of the flow channel of said sample preparation device and said polynucleotide amplification region for lysing said cells, the discharge section of the flow channel of said sample preparation device being in fluid communication with the sample inlet port of said polynucleotide analysis device.

18. The system of claim 17, which further comprises a sample flow channel in said polynucleotide analysis device interconnecting the inlet port of said polynucleotide amplification device and said polynucleotide amplification region at least one of said polynucleotide amplification region and the sample flow channel connected therewith having at least one mesoscale dimension.

19. In combination, the system of claim 11 and an appliance for use with said system, said appliance comprising a holder for said system, a test sample input conduit interfitted with the sample inlet of said sample preparation device and an impellent for moving test sample along the flow passage of said sample preparation device.

20. The combination of claim 19, wherein said appliance further comprising a reservoir for said test sample.

21. In combination, the system of claim 17, and an appliance for use with said system, said appliance comprising a holder for said system, a test sample input conduit interfitted with the sample inlet of said sample preparation device, and an impellent for moving said test sample along the flow passage of said sample preparation device, a carrier fluid input conduit interfitted with said inlet section of the flow channel of said sample preparation device and an impellent for moving said carrier fluid along said flow channel.

22. The combination of claim 21, wherein said appliance further comprises a reservoir for the carrier fluid which is directed into the separation zone of said sample preparation device.

23. The combination of claim 21, wherein said appliance further comprises a detector for detecting a parameter of said test sample in said analyte detection device or said polynucleotide analysis device.

24. A system for performing an analysis of preselected polynucleotide derived from cells, said analysis comprising polynucleotide amplification, said system comprising a sample preparation device according to claim 1 and a device for carrying out polynucleotide amplification which comprises:

a solid substrate fabricated to define:

a sample inlet port; and a flow system comprising:

a polynucleotide amplification region in fluid communication with said inlet port, said polynucleotide amplification region containing reagents for amplifying a polynucleotide, and a sample flow channel in said polynucleotide amplification device interconnecting the inlet port of said polynucleotide amplification device and said polynucleotide amplification region, at least one of said sample flow channel and said polynucleotide amplification region having at least one mesoscale dimension, and lysing means in said flow channel upstream of said polynucleotide amplification region for lysing said cells, the discharge section of the flow channel of said sample preparation device being in fluid communication with the sample inlet port of said polynucleotide amplification device.

25. The system of claim 24, which further comprises, in said polynucleotide amplification device, a sample flow channel of said polynucleotide amplification device interconnecting said inlet port and said polynucleotide amplification region, at least one of said polynucleotide amplification region and the sample flow channel connected thereto having at least one mesoscale dimension.

26. A system for determining an analyte in a fluid sample having particulate components, said system comprising a sample preparation device which comprises a sample flow passage having a sample inlet and an outlet in fluid communication and a separator disposed between said inlet and said outlet, said separator having an upstream-facing portion defining a separation zone in said flow passage in which said particulate components are collected, and an analyte detection device comprising:

a solid substrate fabricated to define:

a sample inlet port; and a flow system comprising:

an analyte detection region in fluid communication with said inlet port, said region containing a reagent which interacts with said analyte to yield a detectable product which is determinative of said analyte, and a detector for detecting said product;

the flow passage outlet of said sample preparation device being in fluid communication with said sample inlet port of said analyte detection device, and at least one of said flow passage and said region having at least one mesoscale dimension.

27. The system of claim 26, which further comprises, in said sample preparation device, a flow channel in fluid communication with said separation zone for affording discharge of collected particulate components from said separation zone, said flow channel having an inlet section for directing a carrier fluid into said separation zone and over the upstream-facing portion of said separator, and a discharge section for directing said carrier fluid from over the upstream-facing portion of said separator and out of said separation zone.

28. The system of claim 27, wherein at least one of the inlet and discharge sections of said flow channel has at least one mesoscale dimension.

* * * * *